US008748137B2

(12) United States Patent
Obata et al.

(10) Patent No.: US 8,748,137 B2
(45) Date of Patent: Jun. 10, 2014

(54) METHOD FOR PRODUCTION OF POLYLACTATE USING RECOMBINANT MICROORGANISM

(75) Inventors: Shusei Obata, Nagoya (JP); Hiromi Kambe, Seto (JP); Masakazu Ito, Toyota (JP); Takashi Shimamura, Toyota (JP); Katsunori Kohda, Nissin (JP); Seiichi Taguchi, Sapporo (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 293 days.

(21) Appl. No.: 13/126,157

(22) PCT Filed: Oct. 27, 2009

(86) PCT No.: PCT/JP2009/068402

§ 371 (c)(1), (2), (4) Date: Apr. 26, 2011

(87) PCT Pub. No.: WO2010/050470

PCT Pub. Date: May 6, 2010

(65) Prior Publication Data

US 2011/0212497 A1 Sep. 1, 2011

(30) Foreign Application Priority Data

Oct. 27, 2008 (JP) ................................ 2008-276185

(51) Int. Cl.

| | |
|---|---|
| ***C12P 7/62*** | (2006.01) |
| ***C12N 9/00*** | (2006.01) |
| ***C12N 9/10*** | (2006.01) |
| ***C12N 1/20*** | (2006.01) |
| ***C12N 15/00*** | (2006.01) |
| ***C07H 21/04*** | (2006.01) |

(52) U.S. Cl.

USPC ........ 435/135; 435/183; 435/193; 435/252.3; 435/320.1; 536/23.2

(58) Field of Classification Search

None

See application file for complete search history.

(56) References Cited

U.S. PATENT DOCUMENTS

| | | | | |
|---|---|---|---|---|
| 5,266,470 | A | 11/1993 | Senior et al. | |
| 5,292,860 | A | 3/1994 | Shiotani et al. | |
| 5,643,758 | A * | 7/1997 | Guan et al. .................. | 435/69.7 |
| 5,981,257 | A | 11/1999 | Fukui et al. | |
| 2004/0076982 | A1 | 4/2004 | Gokarn et al. | |
| 2007/0054386 | A1 | 3/2007 | Taguchi et al. | |

FOREIGN PATENT DOCUMENTS

| | | | |
|---|---|---|---|
| EP | 2 284 261 | A1 | 2/2011 |
| JP | 57-150393 | A | 9/1982 |
| JP | 61-293385 | A | 12/1986 |
| JP | 5-74492 | A | 3/1993 |
| JP | 5-93049 | A | 4/1993 |
| JP | 7-79705 | B2 | 8/1995 |
| JP | 7-265065 | A | 10/1995 |
| JP | 10-108682 | A | 4/1998 |
| JP | 2004-514431 | A | 5/2004 |
| WO | 02/42418 | A2 | 5/2002 |
| WO | 03/100055 | A1 | 12/2003 |
| WO | 2006/126796 | A1 | 11/2006 |
| WO | 2008/062996 | A1 | 5/2008 |
| WO | 2008/062999 | A1 | 5/2008 |
| WO | 2009/031762 | A2 | 3/2009 |

OTHER PUBLICATIONS

Accession CAB77207, Feb. 12, 2002.*

Chica et al. Curr Opin Biotechnol. Aug. 2005;16(4):378-84.*

Sen et al. Appl Biochem Biotechnol. Dec. 2007;143(3):212-23.*

Selmer et al. Eur J Biochem. Jan. 2002;269(1):372-80.*

Accession Q9L3F7. Oct. 1, 2000.*

Accession A0Q1E3, Jan. 9, 2007.*

Accession B1BAC4, Apr. 29, 2008.*

Baba, T et al. Construction of *Escherichia coli* K-12 in-frame single-gene knockout mutants: the Keio collection. Molecular Systems Biology. 2006. p. 1-11.

Coli Genetic Stock Center. Yale University. 2006. p. 1-6.

Pohlmann, A et al. Acety-CoA acetyltransferase (*Ralstonia* eutropha). GenBank YP_725941.1. 2006 p. 1-2.

Pohlmann, A et al. acetoacetyl-CoA reductase (*Ralstonia* eutropha). GenBank YP_726636.1. 2006. p. 1-2.

Selmer, T et al. propionate CoA-transferase (*Clostridium* propionicum). GenBank CAB77207.1. 2002. p. 1-2.

U.S. Office Action dated Nov. 6, 2012 issued in U.S. Appl. No. 12/989,333.

(Continued)

*Primary Examiner* — Christian Fronda

(74) *Attorney, Agent, or Firm* — Sughrue Mion, PLLC

(57) ABSTRACT

It is an object of the present invention to provide a method for efficiently producing a polylactate via microbial fermentation with the use of a sugar as a starting material.

The method is a method for producing a polylactate, which comprises the steps of:

(1) culturing a recombinant microorganism having a protein capable of catalyzing a reaction of transferring CoA to propionic acid and/or lactate and a protein capable of catalyzing a reaction of polyhydroxyalkanoate synthesis consisting of the following amino acid sequence (a) or (b) in a medium containing a carbon source:

(a) an amino acid sequence derived from the amino acid sequence shown in SEQ ID NO: 2 by substitution of at least one of the amino acids at positions 130, 325, 477, and 481 with different amino acid(s); or (b) an amino acid sequence derived from the protein specified in (a) by additional deletion or substitution of one or several amino acid(s) other than the amino acids at positions 130, 325, 477, and 481 or by insertion of one or several amino acid residue(s); and (2) collecting the polylactate from the culture product obtained in step (1).

8 Claims, 10 Drawing Sheets

(56) References Cited

OTHER PUBLICATIONS

Christopher T. Nomura, et al., "PHA Synthase Engineering Toward Superbiocatalysts for Custom-Made Biopolymers", Appl. Microbiol. Biotechnol. 2007, pp. 969-979, vol. 73.

Wei Yuan, et al.,"Class I and III Poyhydroxyalkanoate Synthases from *Ralstonia* Eutropha and Allochromatium Vinosum: Characterization and Substrate Specificity Studies", Archives of Biochemistry and Biophysics, 2001, pp. 87-98, vol. 394. No. 1.

Seiichi Taguchi, et al., "A Microbial Factory for Lactate-Based Polyesters Using a Lactate-Polymerizing Enzyme", Proc. Natl. Acad, Sci. USA, 2008, pp. 17323-17327, vol. 105, No. 45.

Supplementary European Search Report for corresponding EP Patent Application No. 09823580.7 issued on Jul. 5, 2012.

Notice of Allowance issued in U.S. Appl. No. 12/989,333, dated Jun. 13, 2013.

* cited by examiner

C.P-PCT : *C. propionicum*-derived PCT
S.A-PCT : *S. aureus*-derived PCT
M.E-PCT : *M. elsdenii*-derived PCT Cont.: pTV118N
M.E: pTV118N-M.E PCT
C.P: pTV118N-C.P PCT
M.E+C1: pTV118N-PCT-C1(ST/QK)
C.P+C1: pTV118N-C.P PCT-C1(ST/QK)

```
                              SEQUENCE LISTING


<160> NUMBER OF SEQ ID NOS: 6

<210> SEQ ID NO 1
<211> LENGTH: 1677
<212> TYPE: DNA
<213> ORGANISM: Pseudomonas sp.61-3
<220> FEATURE:
<221> NAME/KEY: CDS
<222> LOCATION: (1)..(1677)

<400> SEQUENCE: 1

atg agt aac aag aat agc gat gac ttg aat cgt caa gcc tcg gaa aac       48
Met Ser Asn Lys Asn Ser Asp Asp Leu Asn Arg Gln Ala Ser Glu Asn
1               5                   10                  15

acc ttg ggg ctt aac cct gtc atc ggc ctg cgt gga aaa gat ctg ctg       96
Thr Leu Gly Leu Asn Pro Val Ile Gly Leu Arg Gly Lys Asp Leu Leu
            20                  25                  30

act tct gcc cga atg gtt tta acc caa gcc atc aaa caa ccc att cac      144
Thr Ser Ala Arg Met Val Leu Thr Gln Ala Ile Lys Gln Pro Ile His
        35                  40                  45

agc gtc aag cac gtc gcg cat ttt ggc atc gag ctg aag aac gtg atg      192
Ser Val Lys His Val Ala His Phe Gly Ile Glu Leu Lys Asn Val Met
    50                  55                  60

ttt ggc aaa tcg aag ctg caa ccg gaa agc gat gac cgt cgt ttc aac      240
Phe Gly Lys Ser Lys Leu Gln Pro Glu Ser Asp Asp Arg Arg Phe Asn
65                  70                  75                  80

gac ccc gcc tgg agt cag aac cca ctc tac aaa cgt tat cta caa acc      288
Asp Pro Ala Trp Ser Gln Asn Pro Leu Tyr Lys Arg Tyr Leu Gln Thr
                85                  90                  95

tac ctg gcg tgg cgc aag gaa ctc cac gac tgg atc ggc aac agc aaa      336
Tyr Leu Ala Trp Arg Lys Glu Leu His Asp Trp Ile Gly Asn Ser Lys
            100                 105                 110

ctg tcc gaa cag gac atc aat cgc gct cac ttc gtg atc acc ctg atg      384
Leu Ser Glu Gln Asp Ile Asn Arg Ala His Phe Val Ile Thr Leu Met
        115                 120                 125

acc gaa gcc atg gcc ccg acc aac agt gcg gcc aat ccg gcg gcg gtc      432
Thr Glu Ala Met Ala Pro Thr Asn Ser Ala Ala Asn Pro Ala Ala Val
    130                 135                 140

aaa cgc ttc ttc gaa acc ggc ggt aaa agc ctg ctc gac ggc ctc aca      480
Lys Arg Phe Phe Glu Thr Gly Gly Lys Ser Leu Leu Asp Gly Leu Thr
145                 150                 155                 160

cat ctg gcc aag gac ctg gta aac aac ggc ggc atg ccg agc cag gtg      528
His Leu Ala Lys Asp Leu Val Asn Asn Gly Gly Met Pro Ser Gln Val
                165                 170                 175

gac atg ggc gct ttc gaa gtc ggc aag agt ctg ggg acg act gaa ggt      576
Asp Met Gly Ala Phe Glu Val Gly Lys Ser Leu Gly Thr Thr Glu Gly
            180                 185                 190

gca gtg gtt ttc cgc aac gac gtc ctc gaa ttg atc cag tac cgg ccg      624
Ala Val Val Phe Arg Asn Asp Val Leu Glu Leu Ile Gln Tyr Arg Pro
        195                 200                 205

acc acc gaa cag gtg cat gag cga ccg ctg ctg gtg gtc cca ccg cag      672
Thr Thr Glu Gln Val His Glu Arg Pro Leu Leu Val Val Pro Pro Gln
    210                 215                 220

atc aac aag ttt tat gtg ttt gac ctg agc ccg gat aaa agc ctg gcg      720
Ile Asn Lys Phe Tyr Val Phe Asp Leu Ser Pro Asp Lys Ser Leu Ala
```

```
225                 230                 235                 240

cgc ttc tgc ctg agc aac aac cag caa acc ttt atc gtc agc tgg cgc      768
Arg Phe Cys Leu Ser Asn Asn Gln Gln Thr Phe Ile Val Ser Trp Arg
            245                 250                 255

aac ccg acc aag gcc cag cgt gag tgg ggt ctg tcg act tac atc gat      816
Asn Pro Thr Lys Ala Gln Arg Glu Trp Gly Leu Ser Thr Tyr Ile Asp
        260                 265                 270

gcg ctc aaa gaa gcc gtc gac gta gtt tcc gcc atc acc ggc agc aaa      864
Ala Leu Lys Glu Ala Val Asp Val Val Ser Ala Ile Thr Gly Ser Lys
        275                 280                 285

gac atc aac atg ctc ggc gcc tgc tcc ggt ggc att acc tgc acc gcg      912
Asp Ile Asn Met Leu Gly Ala Cys Ser Gly Gly Ile Thr Cys Thr Ala
    290                 295                 300

ctg ctg ggt cac tac gcc gct ctc ggc gag aag aag gtc aat gcc ctg      960
Leu Leu Gly His Tyr Ala Ala Leu Gly Glu Lys Lys Val Asn Ala Leu
305                 310                 315                 320

acc ctt ttg gtc agc gtg ctc gac acc acc ctc gac tcc cag gtt gca     1008
Thr Leu Leu Val Ser Val Leu Asp Thr Thr Leu Asp Ser Gln Val Ala
            325                 330                 335

ctg ttc gtc gat gag aaa acc ctg gaa gct gcc aag cgt cac tcg tat     1056
Leu Phe Val Asp Glu Lys Thr Leu Glu Ala Ala Lys Arg His Ser Tyr
            340                 345                 350

cag gcc ggc gtg ctg gaa ggc cgc gac atg gcc aaa gtc ttc gcc tgg     1104
Gln Ala Gly Val Leu Glu Gly Arg Asp Met Ala Lys Val Phe Ala Trp
        355                 360                 365

atg cgc cct aac gac ctg atc tgg aac tac tgg gtc aac aac tac ctg     1152
Met Arg Pro Asn Asp Leu Ile Trp Asn Tyr Trp Val Asn Asn Tyr Leu
    370                 375                 380

ctg ggt aac gag cca ccg gtc ttc gac att ctt ttc tgg aac aac gac     1200
Leu Gly Asn Glu Pro Pro Val Phe Asp Ile Leu Phe Trp Asn Asn Asp
385                 390                 395                 400

acc acc cgg ttg cct gct gcg ttc cac ggc gat ctg atc gaa atg ttc     1248
Thr Thr Arg Leu Pro Ala Ala Phe His Gly Asp Leu Ile Glu Met Phe
            405                 410                 415

aaa aat aac cca ctg gtg cgc gcc aat gca ctc gaa gtg agc ggc acg     1296
Lys Asn Asn Pro Leu Val Arg Ala Asn Ala Leu Glu Val Ser Gly Thr
            420                 425                 430

ccg atc gac ctc aaa cag gtc act gcc gac atc tac tcc ctg gcc ggc     1344
Pro Ile Asp Leu Lys Gln Val Thr Ala Asp Ile Tyr Ser Leu Ala Gly
        435                 440                 445

acc aac gat cac atc acg ccc tgg aag tct tgc tac aag tcg gcg caa     1392
Thr Asn Asp His Ile Thr Pro Trp Lys Ser Cys Tyr Lys Ser Ala Gln
    450                 455                 460

ctg ttc ggt ggc aag gtc gaa ttc gtg ctg tcc agc agt ggg cat atc     1440
Leu Phe Gly Gly Lys Val Glu Phe Val Leu Ser Ser Ser Gly His Ile
465                 470                 475                 480

cag agc att ctg aac ccg ccg ggc aat ccg aaa tca cgt tac atg acc     1488
Gln Ser Ile Leu Asn Pro Pro Gly Asn Pro Lys Ser Arg Tyr Met Thr
            485                 490                 495

agc acc gac atg cca gcc acc gcc aac gag tgg caa gaa aac tca acc     1536
Ser Thr Asp Met Pro Ala Thr Ala Asn Glu Trp Gln Glu Asn Ser Thr
            500                 505                 510

aag cac acc gac tcc tgg tgg ctg cac tgg cag gcc tgg cag gcc gag     1584
Lys His Thr Asp Ser Trp Trp Leu His Trp Gln Ala Trp Gln Ala Glu
        515                 520                 525

cgc tcg ggc aaa ctg aaa aag tcc ccg acc agc ctg ggc aac aag gcc     1632
Arg Ser Gly Lys Leu Lys Lys Ser Pro Thr Ser Leu Gly Asn Lys Ala
    530                 535                 540

tat ccg tca gga gaa gcc gcg ccg ggc acg tat gtg cat gaa cgt         1677
Tyr Pro Ser Gly Glu Ala Ala Pro Gly Thr Tyr Val His Glu Arg
```

545 550 555

<210> SEQ ID NO 2
<211> LENGTH: 559
<212> TYPE: PRT
<213> ORGANISM: Pseudomonas sp.61-3

<400> SEQUENCE: 2

Met Ser Asn Lys Asn Ser Asp Asp Leu Asn Arg Gln Ala Ser Glu Asn
1 5 10 15

Thr Leu Gly Leu Asn Pro Val Ile Gly Leu Arg Gly Lys Asp Leu Leu
20 25 30

Thr Ser Ala Arg Met Val Leu Thr Gln Ala Ile Lys Gln Pro Ile His
35 40 45

Ser Val Lys His Val Ala His Phe Gly Ile Glu Leu Lys Asn Val Met
50 55 60

Phe Gly Lys Ser Lys Leu Gln Pro Glu Ser Asp Asp Arg Arg Phe Asn
65 70 75 80

Asp Pro Ala Trp Ser Gln Asn Pro Leu Tyr Lys Arg Tyr Leu Gln Thr
85 90 95

Tyr Leu Ala Trp Arg Lys Glu Leu His Asp Trp Ile Gly Asn Ser Lys
100 105 110

Leu Ser Glu Gln Asp Ile Asn Arg Ala His Phe Val Ile Thr Leu Met
115 120 125

Thr Glu Ala Met Ala Pro Thr Asn Ser Ala Ala Asn Pro Ala Ala Val
130 135 140

Lys Arg Phe Phe Glu Thr Gly Gly Lys Ser Leu Leu Asp Gly Leu Thr
145 150 155 160

His Leu Ala Lys Asp Leu Val Asn Asn Gly Gly Met Pro Ser Gln Val
165 170 175

Asp Met Gly Ala Phe Glu Val Gly Lys Ser Leu Gly Thr Thr Glu Gly
180 185 190

Ala Val Val Phe Arg Asn Asp Val Leu Glu Leu Ile Gln Tyr Arg Pro
195 200 205

Thr Thr Glu Gln Val His Glu Arg Pro Leu Leu Val Val Pro Pro Gln
210 215 220

Ile Asn Lys Phe Tyr Val Phe Asp Leu Ser Pro Asp Lys Ser Leu Ala
225 230 235 240

Arg Phe Cys Leu Ser Asn Asn Gln Gln Thr Phe Ile Val Ser Trp Arg
245 250 255

Asn Pro Thr Lys Ala Gln Arg Glu Trp Gly Leu Ser Thr Tyr Ile Asp
260 265 270

Ala Leu Lys Glu Ala Val Asp Val Val Ser Ala Ile Thr Gly Ser Lys
275 280 285

Asp Ile Asn Met Leu Gly Ala Cys Ser Gly Gly Ile Thr Cys Thr Ala
290 295 300

Leu Leu Gly His Tyr Ala Ala Leu Gly Glu Lys Lys Val Asn Ala Leu
305 310 315 320

Thr Leu Leu Val Ser Val Leu Asp Thr Thr Leu Asp Ser Gln Val Ala
325 330 335

Leu Phe Val Asp Glu Lys Thr Leu Glu Ala Ala Lys Arg His Ser Tyr
340 345 350

Gln Ala Gly Val Leu Glu Gly Arg Asp Met Ala Lys Val Phe Ala Trp
355 360 365

Met Arg Pro Asn Asp Leu Ile Trp Asn Tyr Trp Val Asn Asn Tyr Leu

```
    370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Met Phe
                405                 410                 415

Lys Asn Asn Pro Leu Val Arg Ala Asn Ala Leu Glu Val Ser Gly Thr
            420                 425                 430

Pro Ile Asp Leu Lys Gln Val Thr Ala Asp Ile Tyr Ser Leu Ala Gly
        435                 440                 445

Thr Asn Asp His Ile Thr Pro Trp Lys Ser Cys Tyr Lys Ser Ala Gln
    450                 455                 460

Leu Phe Gly Gly Lys Val Glu Phe Val Leu Ser Ser Ser Gly His Ile
465                 470                 475                 480

Gln Ser Ile Leu Asn Pro Pro Gly Asn Pro Lys Ser Arg Tyr Met Thr
                485                 490                 495

Ser Thr Asp Met Pro Ala Thr Ala Asn Glu Trp Gln Glu Asn Ser Thr
            500                 505                 510

Lys His Thr Asp Ser Trp Trp Leu His Trp Gln Ala Trp Gln Ala Glu
        515                 520                 525

Arg Ser Gly Lys Leu Lys Lys Ser Pro Thr Ser Leu Gly Asn Lys Ala
    530                 535                 540

Tyr Pro Ser Gly Glu Ala Ala Pro Gly Thr Tyr Val His Glu Arg
545                 550                 555


<210> SEQ ID NO 3
<211> LENGTH: 1554
<212> TYPE: DNA
<213> ORGANISM: Megasphaera elsdenii
<220> FEATURE:
<221> NAME/KEY: CDS
<222> LOCATION: (1)..(1554)

<400> SEQUENCE: 3

atg aga aaa gta gaa atc att aca gct gaa caa gca gct cag ctc gta       48
Met Arg Lys Val Glu Ile Ile Thr Ala Glu Gln Ala Ala Gln Leu Val
1               5                   10                  15

aaa gac aac gac acg att acg tct atc ggc ttt gtc agc agc gcc cat       96
Lys Asp Asn Asp Thr Ile Thr Ser Ile Gly Phe Val Ser Ser Ala His
            20                  25                  30

ccg gaa gca ctg acc aaa gct ttg gaa aaa cgg ttc ctg gac acg aac      144
Pro Glu Ala Leu Thr Lys Ala Leu Glu Lys Arg Phe Leu Asp Thr Asn
        35                  40                  45

acc ccg cag aac ttg acc tac atc tat gca ggc tct cag ggt aaa cgc      192
Thr Pro Gln Asn Leu Thr Tyr Ile Tyr Ala Gly Ser Gln Gly Lys Arg
    50                  55                  60

gat ggc cgt gcc gct gaa cat ctg gca cac aca ggc ctt ttg aaa cgc      240
Asp Gly Arg Ala Ala Glu His Leu Ala His Thr Gly Leu Leu Lys Arg
65                  70                  75                  80

gcc atc atc ggt cac tgg cag act gta ccg gct atc ggt aaa ctg gct      288
Ala Ile Ile Gly His Trp Gln Thr Val Pro Ala Ile Gly Lys Leu Ala
                85                  90                  95

gtc gaa aac aag att gaa gct tac aac ttc tcg cag ggc acg ttg gtc      336
Val Glu Asn Lys Ile Glu Ala Tyr Asn Phe Ser Gln Gly Thr Leu Val
            100                 105                 110

cac tgg ttc cgc gcc ttg gca ggt cat aag ctc ggc gtc ttc acc gac      384
His Trp Phe Arg Ala Leu Ala Gly His Lys Leu Gly Val Phe Thr Asp
        115                 120                 125

atc ggt ctg gaa act ttc ctc gat ccc cgt cag ctc ggc ggc aag ctc      432
Ile Gly Leu Glu Thr Phe Leu Asp Pro Arg Gln Leu Gly Gly Lys Leu
```

```
    130                 135                 140

aat gac gta acc aaa gaa gac ctc gtc aaa ctg atc gaa gtc gat ggt      480
Asn Asp Val Thr Lys Glu Asp Leu Val Lys Leu Ile Glu Val Asp Gly
145                 150                 155                 160

cat gaa cag ctt ttc tac ccg acc ttc ccg gtc aac gta gct ttc ctc      528
His Glu Gln Leu Phe Tyr Pro Thr Phe Pro Val Asn Val Ala Phe Leu
                165                 170                 175

cgc ggt acg tat gct gat gaa tcc ggc aat atc acc atg gac gaa gaa      576
Arg Gly Thr Tyr Ala Asp Glu Ser Gly Asn Ile Thr Met Asp Glu Glu
            180                 185                 190

atc ggg cct ttc gaa agc act tcc gta gcc cag gcc gtt cac aac tgt      624
Ile Gly Pro Phe Glu Ser Thr Ser Val Ala Gln Ala Val His Asn Cys
        195                 200                 205

ggc ggt aaa gtc gtc gtc cag gtc aaa gac gtc gtc gct cac ggc agc      672
Gly Gly Lys Val Val Val Gln Val Lys Asp Val Val Ala His Gly Ser
    210                 215                 220

ctg gat ccg cgc atg gtc aaa atc cct ggc atc tat gtc gac tat gtt      720
Leu Asp Pro Arg Met Val Lys Ile Pro Gly Ile Tyr Val Asp Tyr Val
225                 230                 235                 240

gtc gta gct gct ccg gaa gac cat cag cag act tat gac tgc gaa tat      768
Val Val Ala Ala Pro Glu Asp His Gln Gln Thr Tyr Asp Cys Glu Tyr
                245                 250                 255

gat ccg tcc ctt agc ggc gaa cat cgt gct cct gaa ggc gct gct gac      816
Asp Pro Ser Leu Ser Gly Glu His Arg Ala Pro Glu Gly Ala Ala Asp
            260                 265                 270

gca gct ctc ccc atg agc gct aag aaa atc atc ggc cgc cgc ggt gct      864
Ala Ala Leu Pro Met Ser Ala Lys Lys Ile Ile Gly Arg Arg Gly Ala
        275                 280                 285

ttg gaa ttg acc gaa aac gct gtc gtc aac ctc ggc gtc ggc gct ccg      912
Leu Glu Leu Thr Glu Asn Ala Val Val Asn Leu Gly Val Gly Ala Pro
    290                 295                 300

gaa tac gtt gct tcc gtt gcc ggt gaa gaa ggt atc gct gat acc att      960
Glu Tyr Val Ala Ser Val Ala Gly Glu Glu Gly Ile Ala Asp Thr Ile
305                 310                 315                 320

acc ttg acc gtc gaa ggt ggc gct atc ggt ggt gta ccg cag ggc ggt     1008
Thr Leu Thr Val Glu Gly Gly Ala Ile Gly Gly Val Pro Gln Gly Gly
                325                 330                 335

gcc cgc ttc ggt tcg tcc cgt aat gct gat gcc atc atc gac cat act     1056
Ala Arg Phe Gly Ser Ser Arg Asn Ala Asp Ala Ile Ile Asp His Thr
            340                 345                 350

tac cag ttc gac ttc tat gat ggc ggc ggt ctg gac atc gct tac ctc     1104
Tyr Gln Phe Asp Phe Tyr Asp Gly Gly Gly Leu Asp Ile Ala Tyr Leu
        355                 360                 365

ggc ctg gct cag tgc gat ggt tcg ggc aac atc aac gtc agc aag ttc     1152
Gly Leu Ala Gln Cys Asp Gly Ser Gly Asn Ile Asn Val Ser Lys Phe
    370                 375                 380

ggt act aac gtt gcc ggc tgt ggc ggt ttc ccc aac att tcc cag cag     1200
Gly Thr Asn Val Ala Gly Cys Gly Gly Phe Pro Asn Ile Ser Gln Gln
385                 390                 395                 400

aca ccg aat gtt tac ttc tgc ggc acc ttc acg gct ggc ggc ttg aaa     1248
Thr Pro Asn Val Tyr Phe Cys Gly Thr Phe Thr Ala Gly Gly Leu Lys
                405                 410                 415

atc gct gtc gaa gac ggc aaa gtc aag atc ctc cag gaa ggc aaa gcc     1296
Ile Ala Val Glu Asp Gly Lys Val Lys Ile Leu Gln Glu Gly Lys Ala
            420                 425                 430

aag aag ttc atc aaa gct gtc gac cag atc act ttc aac ggt tct tat     1344
Lys Lys Phe Ile Lys Ala Val Asp Gln Ile Thr Phe Asn Gly Ser Tyr
        435                 440                 445

gca gcc cgc aac ggc aaa cat gtt ctc tac atc acg gaa cgc tgc gta     1392
Ala Ala Arg Asn Gly Lys His Val Leu Tyr Ile Thr Glu Arg Cys Val
```

```
    450                 455                 460

ttt gaa ctg acc aaa gaa ggc ttg aaa ctc atc gaa gtc gca ccg ggc      1440
Phe Glu Leu Thr Lys Glu Gly Leu Lys Leu Ile Glu Val Ala Pro Gly
465                 470                 475                 480

atc gat att gaa aaa gat atc ctc gct cac atg gac ttc aag ccg atc      1488
Ile Asp Ile Glu Lys Asp Ile Leu Ala His Met Asp Phe Lys Pro Ile
                485                 490                 495

att gat aat ccg aaa ctc atg gat gcc cgc ctc ttc cag gac ggt ccc      1536
Ile Asp Asn Pro Lys Leu Met Asp Ala Arg Leu Phe Gln Asp Gly Pro
            500                 505                 510

atg gga ctg aaa aaa taa                                              1554
Met Gly Leu Lys Lys
        515


<210> SEQ ID NO 4
<211> LENGTH: 517
<212> TYPE: PRT
<213> ORGANISM: Megasphaera elsdenii

<400> SEQUENCE: 4

Met Arg Lys Val Glu Ile Ile Thr Ala Glu Gln Ala Ala Gln Leu Val
1               5                   10                  15

Lys Asp Asn Asp Thr Ile Thr Ser Ile Gly Phe Val Ser Ser Ala His
            20                  25                  30

Pro Glu Ala Leu Thr Lys Ala Leu Glu Lys Arg Phe Leu Asp Thr Asn
        35                  40                  45

Thr Pro Gln Asn Leu Thr Tyr Ile Tyr Ala Gly Ser Gln Gly Lys Arg
    50                  55                  60

Asp Gly Arg Ala Ala Glu His Leu Ala His Thr Gly Leu Leu Lys Arg
65                  70                  75                  80

Ala Ile Ile Gly His Trp Gln Thr Val Pro Ala Ile Gly Lys Leu Ala
                85                  90                  95

Val Glu Asn Lys Ile Glu Ala Tyr Asn Phe Ser Gln Gly Thr Leu Val
            100                 105                 110

His Trp Phe Arg Ala Leu Ala Gly His Lys Leu Gly Val Phe Thr Asp
        115                 120                 125

Ile Gly Leu Glu Thr Phe Leu Asp Pro Arg Gln Leu Gly Gly Lys Leu
    130                 135                 140

Asn Asp Val Thr Lys Glu Asp Leu Val Lys Leu Ile Glu Val Asp Gly
145                 150                 155                 160

His Glu Gln Leu Phe Tyr Pro Thr Phe Pro Val Asn Val Ala Phe Leu
                165                 170                 175

Arg Gly Thr Tyr Ala Asp Glu Ser Gly Asn Ile Thr Met Asp Glu Glu
            180                 185                 190

Ile Gly Pro Phe Glu Ser Thr Ser Val Ala Gln Ala Val His Asn Cys
        195                 200                 205

Gly Gly Lys Val Val Val Gln Val Lys Asp Val Val Ala His Gly Ser
    210                 215                 220

Leu Asp Pro Arg Met Val Lys Ile Pro Gly Ile Tyr Val Asp Tyr Val
225                 230                 235                 240

Val Val Ala Ala Pro Glu Asp His Gln Gln Thr Tyr Asp Cys Glu Tyr
                245                 250                 255

Asp Pro Ser Leu Ser Gly Glu His Arg Ala Pro Glu Gly Ala Ala Asp
            260                 265                 270

Ala Ala Leu Pro Met Ser Ala Lys Lys Ile Ile Gly Arg Arg Gly Ala
        275                 280                 285
```

```
Leu Glu Leu Thr Glu Asn Ala Val Val Asn Leu Gly Val Gly Ala Pro
    290                 295                 300

Glu Tyr Val Ala Ser Val Ala Gly Glu Glu Gly Ile Ala Asp Thr Ile
305                 310                 315                 320

Thr Leu Thr Val Glu Gly Gly Ala Ile Gly Gly Val Pro Gln Gly Gly
                325                 330                 335

Ala Arg Phe Gly Ser Ser Arg Asn Ala Asp Ala Ile Ile Asp His Thr
            340                 345                 350

Tyr Gln Phe Asp Phe Tyr Asp Gly Gly Gly Leu Asp Ile Ala Tyr Leu
        355                 360                 365

Gly Leu Ala Gln Cys Asp Gly Ser Gly Asn Ile Asn Val Ser Lys Phe
    370                 375                 380

Gly Thr Asn Val Ala Gly Cys Gly Gly Phe Pro Asn Ile Ser Gln Gln
385                 390                 395                 400

Thr Pro Asn Val Tyr Phe Cys Gly Thr Phe Thr Ala Gly Gly Leu Lys
                405                 410                 415

Ile Ala Val Glu Asp Gly Lys Val Lys Ile Leu Gln Glu Gly Lys Ala
            420                 425                 430

Lys Lys Phe Ile Lys Ala Val Asp Gln Ile Thr Phe Asn Gly Ser Tyr
        435                 440                 445

Ala Ala Arg Asn Gly Lys His Val Leu Tyr Ile Thr Glu Arg Cys Val
    450                 455                 460

Phe Glu Leu Thr Lys Glu Gly Leu Lys Leu Ile Glu Val Ala Pro Gly
465                 470                 475                 480

Ile Asp Ile Glu Lys Asp Ile Leu Ala His Met Asp Phe Lys Pro Ile
                485                 490                 495

Ile Asp Asn Pro Lys Leu Met Asp Ala Arg Leu Phe Gln Asp Gly Pro
            500                 505                 510

Met Gly Leu Lys Lys
        515
```

<210> SEQ ID NO 5
<211> LENGTH: 1554
<212> TYPE: DNA
<213> ORGANISM: Staphylococcus aureus

<400> SEQUENCE: 5

```
atgagaaaag tagaaatcat tacagctgaa caagcagctc agctcgtaaa agacaacgac      60

acgattacgt ctatcggctt tgtcagcagc gcccatccgg aagcactgac caaagctttg     120

gaaaaacggt tcctggacac gaacaccccg cagaacttga cctacatcta tgcaggctct     180

cagggtaaac gcgatggccg tgccgctgaa catctggcac acacaggcct tttgaaacgc     240

gccatcatcg gtcactggca gactgtaccg gctatcggta aactggctgt cgaaaacaag     300

attgaagctt acaacttctc gcagggcacg ttggtccact ggttccgcgc cttggcaggt     360

cataagctcg gcgtcttcac cgacatcggt ctggaaactt tcctcgatcc ccgtcagctc     420

ggcggcaagc tcaatgacgt aaccaaagaa gacctcgtca aactgatcga agtcgatggt     480

catgaacagc ttttctaccc gaccttcccg gtcaacgtag ctttcctccg cggtacgtat     540

gctgatgaat ccggcaatat caccatggac gaagaaatcg ggcctttcga aagcacttcc     600

gtagcccagg ccgttcacaa ctgtggcggt aaagtcgtcg tccaggtcaa agacgtcgtc     660

gctcacggca gcctggatcc gcgcatggtc aaaatccctg gcatctatgt cgactatgtt     720

gtcgtagctg ctccggaaga ccatcagcag acttatgact gcgaatatga tccgtccctt     780

agcggcgaac atcgtgctcc tgaaggcgct gctgacgcag ctctccccat gagcgctaag     840
```

```
aaaatcatcg gccgccgcgg tgctttggaa ttgaccgaaa acgctgtcgt caacctcggc    900

gtcggcgctc cggaatacgt tgcttccgtt gccggtgaag aaggtatcgc tgataccatt    960

accttgaccg tcgaaggtgg cgctatcggt ggtgtaccgc agggcggtgc ccgcttcggt   1020

tcgtcccgta atgctgatgc catcatcgac catacttacc agttcgactt ctatgatggc   1080

ggcggtctgg acatcgctta cctcggcctg gctcagtgcg atggttcggg caacatcaac   1140

gtcagcaagt tcggtactaa cgttgccggc tgtggcggtt tccccaacat ttcccagcag   1200

acaccgaatg tttacttctg cggcaccttc acggctggcg gcttgaaaat cgctgtcgaa   1260

gacggcaaag tcaagatcct ccaggaaggc aaagccaaga agttcatcaa agctgtcgac   1320

cagatcactt tcaacggttc ttatgcagcc cgcaacggca aacatgttct ctacatcacg   1380

gaacgctgcg tatttgaact gaccaaagaa ggcttgaaac tcatcgaagt cgcaccgggc   1440

atcgatattg aaaaagatat cctcgctcac atggacttca agccgatcat tgataatccg   1500

aaactcatgg atgcccgcct cttccaggac ggtcccatgg gactgaaaaa ataa         1554
```

<210> SEQ ID NO 6
<211> LENGTH: 517
<212> TYPE: PRT
<213> ORGANISM: Staphylococcus aureus

<400> SEQUENCE: 6

```
Met Arg Lys Val Glu Ile Ile Thr Ala Glu Gln Ala Ala Gln Leu Val
1               5                   10                  15

Lys Asp Asn Asp Thr Ile Thr Ser Ile Gly Phe Val Ser Ser Ala His
            20                  25                  30

Pro Glu Ala Leu Thr Lys Ala Leu Glu Lys Arg Phe Leu Asp Thr Asn
        35                  40                  45

Thr Pro Gln Asn Leu Thr Tyr Ile Tyr Ala Gly Ser Gln Gly Lys Arg
    50                  55                  60

Asp Gly Arg Ala Ala Glu His Leu Ala His Thr Gly Leu Leu Lys Arg
65                  70                  75                  80

Ala Ile Ile Gly His Trp Gln Thr Val Pro Ala Ile Gly Lys Leu Ala
                85                  90                  95

Val Glu Asn Lys Ile Glu Ala Tyr Asn Phe Ser Gln Gly Thr Leu Val
            100                 105                 110

His Trp Phe Arg Ala Leu Ala Gly His Lys Leu Gly Val Phe Thr Asp
        115                 120                 125

Ile Gly Leu Glu Thr Phe Leu Asp Pro Arg Gln Leu Gly Gly Lys Leu
    130                 135                 140

Asn Asp Val Thr Lys Glu Asp Leu Val Lys Leu Ile Glu Val Asp Gly
145                 150                 155                 160

His Glu Gln Leu Phe Tyr Pro Thr Phe Pro Val Asn Val Ala Phe Leu
                165                 170                 175

Arg Gly Thr Tyr Ala Asp Glu Ser Gly Asn Ile Thr Met Asp Glu Glu
            180                 185                 190

Ile Gly Pro Phe Glu Ser Thr Ser Val Ala Gln Ala Val His Asn Cys
        195                 200                 205

Gly Gly Lys Val Val Val Gln Val Lys Asp Val Val Ala His Gly Ser
    210                 215                 220

Leu Asp Pro Arg Met Val Lys Ile Pro Gly Ile Tyr Val Asp Tyr Val
225                 230                 235                 240

Val Val Ala Ala Pro Glu Asp His Gln Gln Thr Tyr Asp Cys Glu Tyr
                245                 250                 255
```

-continued

```
Asp Pro Ser Leu Ser Gly Glu His Arg Ala Pro Glu Gly Ala Ala Asp
            260                 265                 270

Ala Ala Leu Pro Met Ser Ala Lys Lys Ile Ile Gly Arg Arg Gly Ala
        275                 280                 285

Leu Glu Leu Thr Glu Asn Ala Val Val Asn Leu Gly Val Gly Ala Pro
    290                 295                 300

Glu Tyr Val Ala Ser Val Ala Gly Glu Glu Gly Ile Ala Asp Thr Ile
305                 310                 315                 320

Thr Leu Thr Val Glu Gly Gly Ala Ile Gly Gly Val Pro Gln Gly Gly
                325                 330                 335

Ala Arg Phe Gly Ser Ser Arg Asn Ala Asp Ala Ile Ile Asp His Thr
            340                 345                 350

Tyr Gln Phe Asp Phe Tyr Asp Gly Gly Gly Leu Asp Ile Ala Tyr Leu
        355                 360                 365

Gly Leu Ala Gln Cys Asp Gly Ser Gly Asn Ile Asn Val Ser Lys Phe
    370                 375                 380

Gly Thr Asn Val Ala Gly Cys Gly Gly Phe Pro Asn Ile Ser Gln Gln
385                 390                 395                 400

Thr Pro Asn Val Tyr Phe Cys Gly Thr Phe Thr Ala Gly Gly Leu Lys
                405                 410                 415

Ile Ala Val Glu Asp Gly Lys Val Lys Ile Leu Gln Glu Gly Lys Ala
            420                 425                 430

Lys Lys Phe Ile Lys Ala Val Asp Gln Ile Thr Phe Asn Gly Ser Tyr
        435                 440                 445

Ala Ala Arg Asn Gly Lys His Val Leu Tyr Ile Thr Glu Arg Cys Val
    450                 455                 460

Phe Glu Leu Thr Lys Glu Gly Leu Lys Leu Ile Glu Val Ala Pro Gly
465                 470                 475                 480

Ile Asp Ile Glu Lys Asp Ile Leu Ala His Met Asp Phe Lys Pro Ile
                485                 490                 495

Ile Asp Asn Pro Lys Leu Met Asp Ala Arg Leu Phe Gln Asp Gly Pro
            500                 505                 510

Met Gly Leu Lys Lys
        515
```

METHOD FOR PRODUCTION OF POLYLACTATE USING RECOMBINANT MICROORGANISM

CROSS REFERENCE TO RELATED APPLICATIONS

This application is a National Stage of International Application No. PCT/JP2009/068402 filed Oct. 27, 2009, claiming priority based on Japanese Patent Application No. 2008-276185, filed Oct. 27, 2008, the contents of all of which are incorporated herein by reference in their entirety.

TECHNICAL FIELD

The present invention relates to a method for producing a polylactate using a recombinant microorganism.

BACKGROUND ART

In view of global environmental issues, biologically derived polyesters have been gaining attention as biodegradable plastics that can be readily degraded in nature or as "green" plastics that can be synthesized from renewable carbon resources such as sugars or plant oils. In particular, polylactates can be obtained at relatively low cost. The melting points thereof are 170° C. or higher. Therefore, polylactates have sufficient heat resistance and thus can be shaped by melt molding. Accordingly, polylactates have been expected to be used as highly practical biodegradable polymers.

However, polylactate production has been conventionally carried out by neutralizing and purifying lactic acid produced by microorganisms, forming a dimeric cyclic compound (lactide), and carrying out polymerization as described in JP Patent Publication (Kokai) No. 2004-204464 A, which is problematic in terms of cost.

Hitherto, many microorganisms have been reported to have the ability to produce a polyester using a sugar as a carbon source (Non-Patent Document 1). A representative example of a biodegradable plastic produced by a microorganism is poly-3-hydroxybutyrate (polyhydroroxybutyrate (PHB)) consisting of 3-hydroxybutyrate (3βB) monomers. PHB is a thermoplastic polymer having a melting temperature of approximately 180° C. PHB has excellent melting processability as well as biodegradability, which is advantageous. At the same time, PHB is hard and fragile because of its high crystallinity. That is to say, it has poor shock resistance, which is problematic in terms of physical properties.

As a method for solving problems regarding physical properties of PHB, a method for producing a polyester copolymer consisting of 3HB and a different hydroxyalkanoate using a microorganism has been developed.

For example, Patent Document 1 discloses a method for producing a copolymer consisting of 3HB and 3-hydroxyvalerate (3HV). In addition, Patent Document 2 discloses a method for producing a copolymer consisting of 3HB and 3HV by allowing a microorganism of the genus *Methylobacterium* (*Methylobacterium* sp.), *Paracoccus* (*Paracoccus* sp.), *Alcaligenes* (*Alcaligenes* sp.), or *Pseudomonas* (*Pseudomonas* sp.) to come into contact with a primary alcohol having a carbon number of 3 to 7.

Such copolymer consisting of 3HB and 3HV has a higher degree of flexibility than PHB. In addition, it has been confirmed that an increase in the 3HV content in a polyester copolymer results in enhanced flexibility. In the above method for producing a copolymer consisting of 3HB and 3HV using a microorganism, the 3HV content in a polyester copolymer is regulated by adding, for example, propionic acid in the case of Patent Document 1 or propane-1-ol in the case of Patent Document 3 to a medium.

For instance, P(3HB-co-3HH), which is a two-component polyester copolymer consisting of 3HB and 3-hydroxyhexanoate (hereinafter abbreviated as "3HH"), and a method for producing the same are disclosed in Patent Documents 4 and 5. In the methods for producing a P(3HB-co-3HH) copolymer disclosed in these Patent Documents, fermentative production from a fatty acid such as oleic acid or fat and oil such as olive oil is carried out using *Aeromonas caviae* isolated from the soil. In addition, it has been reported that a recombinant strain is obtained by cloning the PHA synthase gene from *A. caviae* and introducing the cloned gene into *Alcaligenes eutrophus* for production of P(3HB-co-3HH) with the use of fatty acid as a carbon source and the recombinant strain (Patent Document 6).

In addition, in any case of the above methods for producing a polyester copolymer using a microorganism, it is necessary to use a polyhydroxyalkanoate synthase, which is an enzyme protein having activity of directly synthesizing a polymer. In addition, it has been attempted to modify such synthase so as to control the monomer unit mole fraction. For example, Patent Document 7 discloses a mutant enzyme capable of producing PHB with a high 3HB content, which is obtained by modifying the amino acid sequence of a polyhydroxyalkanoate synthase of a microorganism that has been identified as *Pseudomonas* sp. 61-3.

Meanwhile, a polyester copolymer consisting of a non-3-hydroxyalkanoate component serving as a monomer unit is expected to have physical properties differing from those of the above polyester copolymer. Patent Document 8 discloses a method for producing, as an example of such polyester copolymer comprising a non-3-hydroxyalkanoate component serving as a monomer unit, a polyester copolymer consisting of 3HB and lactate (LA) by culturing *Ralstonia eutropha* (previous name: *Alcaligenes eutrophus*) incorporating the nucleic acid encoding propionyl-CoA transferase of *Clostridium propionicum* with the addition of lactate to a medium. The document further discloses a method for producing a copolymer consisting of 3-hydroxyhexanoate, 3-hydroxyoctanoate, 3-hydroxydecanoate, and lactate by culturing *Escherichia coli* incorporating the nucleic acid encoding *C. propionium*-derived propionyl-CoA transferase and the nucleic acid encoding *Pseudomonas* sp. 61-3-derived polyhydroxyalkanoate synthase with addition of lactate and decenoic acid to a medium.

In the above, a polyester copolymer consisting of 3-hydroxyalkanoate serving as a monomer unit, a polyester copolymer consisting of a non-3-hydroxyalkanoate component serving as a monomer unit, and a method for producing the same using a microorganism are described.

However, there have not been any reports of methods for efficiently producing polylactate via microbial fermentation with the use of sugar as a starting material.

Non-Patent Document 1: "Biodegradable Plastic Handbook," Biodegradable Plastics Society, 1995, pp. 178-197, (published by NTS Inc.)

Patent Document 1: JP Patent Publication (Kokai) No. 57-150393 A (1982)

Patent Document 2: JP Patent Publication (Kokai) No. 5-74492 A (1993)

Patent Document 3: JP Patent Publication (Kokoku) No. 7-79705 B (1995)

Patent Document 4: JP Patent Publication (Kokai) No. 5-93049 A (1993)

Patent Document 5: JP Patent Publication (Kokai) No. 7-265065 A (1995)
Patent Document 6: JP Patent Publication (Kokai) No. 10-108682 A (1998)
Patent Document 7: WO2003/100055
Patent Document 8: WO2006/126796

DISCLOSURE OF THE INVENTION

Problem to be Solved by the Invention

It is an object of the present invention to provide a method for efficiently producing a polylactate via microbial fermentation with the use of a sugar as a starting material.

Means for Solving Problem

The present inventors found that a recombinant microorganism disclosed in Patent Document 7 into which the nucleic acid encoding the polyhydroxyalkanoate synthase mutant has been introduced can efficiently produce a polylactate directly from a sugar. This has led to the completion of the following inventions.

(1) A method for producing a polylactate, which comprises the steps of:

(1) culturing a recombinant microorganism having a protein capable of catalyzing a reaction of transferring CoA to propionic acid and/or lactate and a protein capable of catalyzing a reaction of polyhydroxyalkanoate synthesis consisting of the following amino acid sequence (a) or (b) in a medium containing a carbon source:

(a) an amino acid sequence derived from the amino acid sequence shown in SEQ ID NO: 2 by substitution of at least one of the amino acids at positions 130, 325, 477, and 481 with different amino acid(s); or (b) an amino acid sequence derived from the protein specified in (a) by additional deletion or substitution of one or several amino acid(s) other than the amino acids at positions 130, 325, 477, and 481 or by insertion of one or several amino acid residue(s); and (2) collecting the polylactate from the culture product obtained in step (1).

(2) The production method according to (1), wherein the amino acid sequence of the protein capable of catalyzing a reaction of transferring CoA to propionic acid and/or lactate is the amino acid sequence shown in SEQ ID NO: 4 or an amino acid sequence derived from the amino acid sequence shown in SEQ ID NO: 4 by deletion, substitution, or addition of one or several amino acid(s).

(3) The production method according to (1), wherein the amino acid sequence of the protein capable of catalyzing a reaction of transferring CoA to propionic acid and/or lactate is the amino acid sequence shown in SEQ ID NO: 6 or an amino acid sequence derived from the amino acid sequence shown in SEQ ID NO: 6 by deletion, substitution, or addition of one or several amino acid(s).

(4) The production method according to (1), wherein the amino acid sequence of the protein capable of catalyzing a reaction of polyhydroxyalkanoate synthesis is an amino acid sequence derived from the amino acid sequence shown in SEQ ID NO: 2 by substitution of amino acids at positions 325 and 481 with different amino acids.

(5) The production method according to (1), wherein the amino acid sequence of the protein capable of catalyzing a reaction of polyhydroxyalkanoate synthesis is an amino acid sequence derived from the amino acid sequence shown in SEQ ID NO: 2 by substitution of Ser at position 325 with Thr and Gln at position 481 with Lys.

(6) The production method according to (1), wherein any one of the proteins is a protein encoded by a recombinant expression vector introduced into a microorganism.

(7) A recombinant microorganism having a protein capable of catalyzing a reaction of transferring CoA to propionic acid and/or lactate and a protein capable of catalyzing a reaction of polyhydroxyalkanoate synthesis consisting of the following amino acid sequence (a) or (b):

(a) an amino acid sequence derived from the amino acid sequence shown in SEQ ID NO: 2 by substitution of at least one of the amino acids at positions 130, 325, 477, and 481 with different amino acid(s); or (b) an amino acid sequence derived from the protein specified in (a) by additional deletion or substitution of one or several amino acid(s) other than the amino acids at positions 130, 325, 477, and 481 or by insertion of one or several amino acid residue(s).

(8) The recombinant microorganism according to (7) wherein the amino acid sequence of the protein capable of catalyzing a reaction of transferring CoA to propionic acid and/or lactate is the amino acid sequence shown in SEQ ID NO: 4 or an amino acid sequence derived from the amino acid sequence shown in SEQ ID NO: 4 by deletion, substitution, or addition of one or several amino acid(s).

(9) The recombinant microorganism according to (7), wherein the amino acid sequence of the protein capable of catalyzing a reaction of transferring CoA to propionic acid and/or lactate is the amino acid sequence shown in SEQ ID NO: 6 or an amino acid sequence derived from the amino acid sequence shown in SEQ ID NO: 6 by deletion, substitution, or addition of one or several amino acid(s).

(10) The recombinant microorganism according to (7), wherein the amino acid sequence of the protein capable of catalyzing a reaction of polyhydroxyalkanoate synthesis is an amino acid sequence derived from the amino acid sequence shown in SEQ ID NO: 2 by substitution of amino acids at positions 325 and 481 with different amino acids.

(11) The recombinant microorganism according to (7), wherein the amino acid sequence of a protein capable of catalyzing a reaction of polyhydroxyalkanoate synthesis is an amino acid sequence derived from the amino acid sequence shown in SEQ ID NO: 2 by substitution of Ser at position 325 with Thr and Gln at position 481 with Lys.

(12) The recombinant microorganism according to (7), into which a recombinant expression vector having a gene encoding any one of the proteins is introduced.

This description includes part or all of the contents as disclosed in the description and/or drawings of Japanese Patent Application No. 2008-276185, which is a priority document of the present application.

Effects of the Invention

According to the production method of the present invention, a polylactate can be efficiently produced using an inexpensive carbon source as a starting material, and thus the production cost of a biodegradable plastic can be reduced.

BEST MODE FOR CARRYING OUT THE INVENTION

Figure 1:
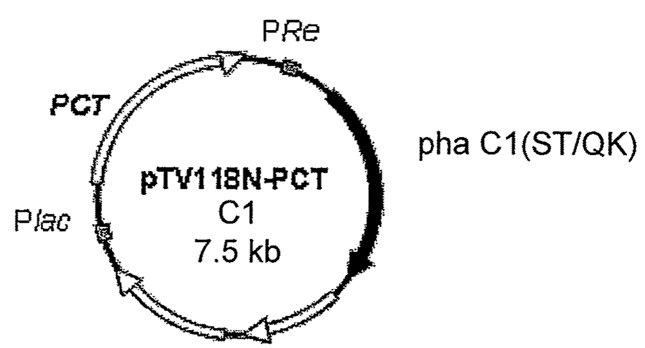
FIG. 1 schematically shows the configuration of a recombinant plasmid pTV118NPCTC1(ST/QK). In the figure, "phaC1(ST/QK)" denotes the STQK gene, "PCT" denotes the *M. elsdenii*-derived PCT gene, "PRe" denotes an *R. eutropha*-derived promoter, and "Plac" denotes an *Escherichia coli* lactose operon promoter.

The present invention relates to a method for producing a polylactate, which comprises the steps of:

(1) culturing a recombinant microorganism having a protein capable of catalyzing a reaction of transferring CoA to propionic acid and/or lactate and a protein capable of catalyzing a reaction of polyhydroxyalkanoate synthesis consisting of the following amino acid sequence (a) or (b) in a medium containing a carbon source:

(a) an amino acid sequence derived from the amino acid sequence shown in SEQ ID NO: 2 by substitution of at least one of the amino acids at positions 130, 325, 477, and 481 with different amino acid(s); or (b) an amino acid sequence derived from the protein specified in (a) by additional deletion or substitution of one or several amino acid(s) other than the amino acids at positions 130, 325, 477, and 481 or by insertion of one or several amino acid residue(s); and (2) collecting the polylactate from the culture product obtained in step (1). Hereinafter, proteins and recombinant microorganisms used in the present invention and conditions for the production method of the present invention are described.

[1] A Protein Capable of Catalyzing a Reaction of Transferring CoA to Propionic Acid and/or Lactate (LA)

A "protein capable of catalyzing a reaction of transferring CoA to propionic acid and/or LA" used in the present invention is a protein having activity of catalyzing a reaction of transferring CoA from an appropriate CoA substrate to propionic acid and/or LA. The protein having such activity is generally referred to as propionyl-CoA transferase (PCT). Hereinafter, the protein is denoted by "PCT" in the present invention.

Table 1 shows representative examples of PCT origins (microorganism names) that have been reported in the past and information on references disclosing the nucleotide sequences encoding the microorganisms.

TABLE 1

| Microorganism name | Reference information |
|---|---|
| *Clostridium propionicum* | Eur. J. Biochem., 2002, Vol. 269, pp. 372-380 |
| *Megasphaera elsdenii* | U.S. Pat. No. 7,186,541 |
| *Staphylococcus aureus* | Eur. J. Biochem., 2002, Vol. 269, pp. 372-380 |
| *Escherichia coli* | Eur. J. Biochem., 2002, Vol. 269, pp. 372-380 |

In addition to the above examples shown in table 1, any PCT that has been reported in the past can be used in the present invention. In addition, as long as a "protein capable of catalyzing a reaction of transferring CoA to propionic acid and/or LA" is used, even a protein consisting of an amino acid sequence derived from the amino acid sequence of a known PCT by deletion, substitution, or addition of one or several amino acid(s) can be used. Here, the term "more amino acids" used in connection with the PCT amino acid sequence refers to 1 to 50 amino acids, preferably 1 to 25 amino acids, and more preferably 10 or less amino acids.

Catalytic activity in a reaction of transferring CoA to propionic acid and/or LA can be determined according to, for example, the method described by A. E. Hofmeister et al. (Eur. J. Biochem., vol. 206, pp. 547-552).

A preferable example of PCT in the present invention is *Megasphaera elsdenii*-derived PCT. The amino acid sequence thereof is shown in SEQ ID NO: 4. An example of the nucleotide sequence of nucleic acid (DNA) encoding the amino acid sequence is shown in SEQ ID NO: 3.

Another example of a preferable PCT in the present invention is *Staphylococcus aureus*-derived PCT. The amino acid sequence of *Staphylococcus aureus*-derived PCT is shown in SEQ ID NO: 6. An example of the nucleotide sequence of a nucleic acid (DNA) encoding the amino acid sequence is shown in SEQ ID NO: 5. As described in the Examples below, *Staphylococcus aureus*-derived PCT is superior to *Megasphaera elsdenii*-derived PCT in terms of lactate CoA productivity in the early phase of microbial culture. This suggests that lactate CoA and a polylactate can be more rapidly produced. Accordingly, the use of *Staphylococcus aureus*-derived PCT is advantageous in that the cost of polylactate production can be reduced.

In the present invention, any of the above types of PCTs may be used alone, or PCTs from a plurality of species may be used in combination. For instance, *Megasphaera elsdenii*-derived PCT is superior to *Staphylococcus aureus*-derived PCT in terms of lactateCoA productivity in the late phase of microbial culture. It is thought that the combined use of both PCTs allows maintenance of lactate CoA productivity for a longer time period than previously possible, based on such characteristics of *Megasphaera elsdenii*-derived PCT and the aforementioned characteristics of *Staphylococcus aureus*-derived PCT.

[2] A Protein Capable of Catalyzing a Reaction of Polyhydroxyalkanoate Synthesis The protein capable of catalyzing polyhydroxyalkanoate synthesis of the present invention is a protein consisting of:

(a) an amino acid sequence derived from the amino acid sequence shown in SEQ ID NO: 2 by substitution of at least one of amino acids at positions 130, 325, 477, and 481 with different amino acid(s); or (b) an amino acid sequence derived from the protein specified in (a) by additional deletion or substitution of one or several amino acid(s) other than the amino acids at positions 130, 325, 477, and 481 or by insertion of one or several amino acid residue(s). A protein defined in (a) is obtained by partially mutating the amino acid sequence of *Pseudomonas* species (*Pseudomonas* sp.) 61-3-derived polyhydroxyalkanoate synthase described in Patent Document 7. A protein defined in (b) is obtained by additionally mutating a protein defined in (a) to an extent such that the activity of the protein defined in (a) can be maintained. In addition, the term "more amino acids" used in connection with the protein defined in (b) refers to 1 to 50 amino acids, preferably 1 to 25 amino acids, and more preferably 10 or fewer amino acids. Hereinafter, a protein capable of catalyzing polyhydroxyalkanoate synthesis of the present invention is referred to as "PhaCm." In addition, Patent Document 7 is incorporated herein by reference in its entirety.

Preferable examples of PhaCm include a single mutant protein obtained by substitution of any one of the amino acids at positions 130, 325, 477, and 481 of the amino acid sequence shown in SEQ ID NO: 2 listed in table 6 or 7 in Patent Document 7, a double mutant protein obtained by substitution of any two of the same, a triple mutant protein obtained by substitution of any three of the same, and a quadruple mutant protein obtained by substitution of all four of the same.

A preferable protein is a double mutant protein obtained by substitution of any two of the above. A particularly preferable protein is a double mutant protein obtained by substitution of Ser at position 325 with Thr and Gln at position 481 with Lys (hereinafter abbreviated as "STQK").

DNA encoding PhaCm can be produced via recombination by a site-specific mutagenesis method known to persons skilled in the art based on the amino acid sequence (SEQ ID NO: 2) of a polyhydroxyalkanoate synthase from *Pseudomonas* species (*Pseudomonas* sp.) 61-3 and the nucleotide sequence (SEQ ID NO: 1) of DNA encoding the same. In addition, as described in Patent Document 7, the PhaCm activity of catalyzing polyhydroxyalkanoate synthesis can be confirmed by obtaining a host cell via transformation with the above nucleic acid capable of expressing PhaCm and examining the polyhydroxyalkanoate accumulation capacity of the host cell.

[3] Nucleic Acids Encoding the Proteins

The nucleic acids encoding proteins (1) and (2) described above are introduced into microorganisms, followed by protein transcription and translation therein. The thus obtained proteins are preferably used. Each nucleic acid to be introduced into a microorganism is preferably incorporated into a vector.

A vector for introducing the aforementioned nucleic acid into a microorganism may be a vector that can autonomously replicate in a host. Preferable examples thereof include plasmid DNA and phage DNA. Examples of a vector for introducing a nucleic acid into *Escherichia coli* include: plasmid DNAs such as pBR322, pUC18, and pBLuescriptII; and phage DNAs such as EMBL3, M13, and λgtII. In addition, examples of a vector used for introduction into yeast include YEp13 and YCp50.

In addition, examples of a vector used for introduction of a nucleic acid into a microorganism of the genus *Ralstonia* or *Pseudomonas* include pLA2917(ATCC37355) having an RK2 replication origin and pJRD215 (ATCC 37533) having an RSF1010 replication origin, which can be replicated/conserved in a wide range of hosts.

The nucleic acids (preferably DNAs) encoding proteins (1) and (2) described above can be inserted into vectors by a gene recombination technique known to persons skilled in the art. In addition, upon recombination, it is preferable to ligate DNA (inserted into a vector) downstream of a promoter that can control transcription/translation of a relevant protein from the DNA. Any promoter can be used as long as it can control gene transcription in a host. For instance, when *Escherichia coli* is used as a host, a trp promoter, a lac promoter, a PL promoter, a PR promoter, a T7 promoter, or the like can be used. In addition, when yeast is used as a host, a gal1 promoter, a gal10 promoter, or the like can be used. Further, when a microorganism of the genus *Pseudomonas* is used as the microorganism of the present invention, a region such as the region that is supposed to contain a promoter located upstream of the phaC1Ps gene or the phbCRe operon can be used as a promoter.

In addition, if necessary, the vector of the present invention can be ligated to a terminator sequence, an enhancer sequence, a splicing signal sequence, a polyA addition signal sequence, a ribosome binding sequence (SD sequence), and a selection marker gene, which can be used in a microorganism into which a nucleic acid is introduced. Examples of a selection marker gene include: a gene involved in intracellular biosynthesis of a nutrient such as an amino acid or a nucleic acid and a gene encoding a fluorescent protein such as luciferase, in addition to a drug-resistant gene such as an ampicillin-resistant gene, a tetracycline-resistant gene, a neomycin-resistant gene, a kanamycin-resistant gene, or a chloramphenicol-resistant gene.

Any aforementioned nucleic acid, which is preferably incorporated into a vector, is introduced into a microorganism by a method known to persons skilled in the art. Examples of a method for recombination of a vector into a microorganism include a calcium phosphate method, an electroporation method, a spheroplast method, a lithium acetate method, a conjugational transfer method, and a method using calcium ions.

[4] Microorganism

The recombinant microorganism of the present invention is a microorganism expressing proteins (1) and (2) described above, and it is preferably a microorganism transformed via introduction of the nucleic acids capable of functionally expressing proteins (1) and (2). Preferable examples of such microorganism include bacteria of the genus *Pseudomonas* such as the *Pseudomonas* sp. 61-3 strain, bacteria of the genus *Ralstonia* such as *R. eutropha*, bacteria of the genus *Bacillus* such as *Bacillus subtilis*, bacteria of the genus *Escherichia* such as *Escherichia coli*, bacteria of the genus *Corynebacterium*, yeasts of the genus *Saccharomyces* such as *Saccharomyces cerevisiae*, and yeasts of the genus *Candida* such as *Candida maltosa*. Of these, *Escherichia coli*, bacteria of the genus *Corynebacterium*, and *R. eutropha* are preferable. *Escherichia coli* and bacteria of the genus *Corynebacterium* are particularly preferable.

In the case of a microorganism such as *R. eutropha*, which originally contains a unique polyhydroxyalkanoate synthase, a microorganism lacking the capacity to express such unique polyhydroxyalkanoate synthase is preferably used. Such microorganism lacking expression capacity can be produced by treating a microorganism with a chemical mutation source such as nitrosoguanidine or a physical mutation source such as UV radiation, introducing a mutant nucleic acid (obtained by modifying a nucleic acid encoding a polyhydroxyalkanoate synthase so as not to cause the functional expression of the enzyme) into a microorganism, or inducing “homologous recombination.” Destruction of the polyhydroxyalkanoate synthase gene can be confirmed by examining whether a hybridizing band shifts to the expected position when compared with a wild-type strain-derived band upon Southern hybridization with the use of a portion of the gene as a probe.

[5] Production of a Polylactate

A polylactate can be produced by culturing a recombinant microorganism into which any aforementioned nucleic acid has been introduced in a medium containing a carbon source, causing generation and accumulation of a polylactate in cultured microbial cells or a culture product, and collecting the polylactate from the cultured microbial cells or the culture product.

Preferably, each recombinant microorganism of the present invention is cultured under general culture conditions for the microorganism depending on the recombinant microorganism type, except for the medium composition.

A medium with a specific composition is not particularly required herein. However, it is preferable to use a medium with the limited content of a nitrogen source (other than a carbon source), an inorganic salt, or a different organic nutrient. An example of a medium for culturing a recombinant microorganism obtained by incorporating a nucleic acid into a bacterium of the genus *Ralstonia* or *Pseudomonas* is a medium with the nitrogen source content limited to 0.01% to 0.1%.

Examples of a carbon source include carbohydrates such as glucose, fructose, sucrose, and maltose. In addition, a fat-and-oil-related substance with a carbon number of 4 or higher can be used as a carbon source. Examples of a fat-and-oil-related substance with a carbon number of 4 or higher include: natural fat and oil such as corn oil, soybean oil, safflower oil, sunflower oil, olive oil, coconut oil, palm oil, rapeseed oil, fish oil, whale oil, lard, or beef tallow; fatty acid such as butanoic acid, pentanoic acid, hexanoic acid, octanoic acid, decanoic acid, lauric acid, oleic acid, palmitic acid, linolenic acid, linoleic acid, or myristic acid, or an ester of such fatty acid, and alcohol such as octanol, lauryl alcohol, oleyl alcohol, or palmityl alcohol, or an ester of such alcohol.

Examples of a nitrogen source include peptone, meat extract, yeast extract, and corn steep liquor, in addition to ammonium salts such as ammonia, ammonium chloride, ammonium sulfate, and ammonium phosphate. Examples of an inorganic substance include primary potassium phosphate, secondary potassium phosphate, magnesium phosphate, magnesium sulfate, and sodium chloride.

Preferably, culture is carried out under aerobic conditions via general shake culture or the like at 25° C. to 37° C. within 24 hours or longer after transcriptional expression of proteins [1] and [2] described above. During culture, an antibiotic such as kanamycin, ampicillin, or tetracycline may be added to a medium. If all or some of the DNAs encoding proteins [1] and [2] are ligated under the regulation of an inducible promoter, a factor that induces transcription of the promoter may be added to a medium.

In one preferable embodiment of the present invention, the method for producing a polylactate comprises culturing recombinant *Escherichia coli* into which an expression vector containing the nucleic acid encoding *M. elsdenii*-derived PCT (SEQ ID NO: 3) or the nucleic acid encoding *S. aureus*-derived PCT (SEQ ID NO: 5) and the nucleic acid encoding STQK has been introduced. According to the method of the present invention, a polylactate can be produced from inexpensive blackstrap molasses without the addition of a monomer component (e.g., LA) that constitutes a polymer of interest to a medium. This is advantageous in terms of production cost.

In the present invention, a polylactate can be collected by a method for collecting a polylactate or PHA from a microorganism that is known to persons skilled in the art. For example, microbial cells are collected from a culture solution via centrifugation, followed by washing and drying. Then, the dried microbial cells are suspended in chloroform and heated for extraction of a polyester of interest in a chloroform fraction. Further, methanol is added to the resulting chloroform solution for precipitation of a polylactate. The supernatant is removed via filtration or centrifugation, followed by drying. Thus, the purified polylactate can be obtained.

It is possible to confirm whether the collected polyester is a polylactate by a general method such as gas chromatography or a nuclear magnetic resonance method.

The present invention is described below in more detail with reference to the Examples in a non-limited manner. In addition, experimental operations used in the Examples were conducted according to manuals introducing experimental operations (e.g., Sambrook et al., Molecular cloning: a laboratory manual, 2nd ed. 1989, Cold Spring Harbor Laboratory Press, Cold Spring Harbor, N.Y.) and instructions included with a variety of reagents and kits.

EXAMPLES

Example 1

(1) Production of a Recombinant Microorganism

Genomic DNA was extracted from *M. elsdenii* (ATCC17753) with the use of a DNeasy Tissue Kit (Qiagen). Subsequently, primer DNA of a forward primer comprising the EcoRI recognition sequence and that of a reverse primer comprising the PstI recognition sequence were synthesized in order to amplify a nucleic acid encoding propionyl CoA transferase (accession No. J04987) by PCR.

PCR reaction was performed for 1 cycle of 94° C. for 2 minutes and 30 cycles of 94° C. for 15 seconds, 55° C. for 30 seconds, and 68° C. for 2 minutes in a reaction solution containing KOD-Plus-DNA polymerase (1 U), PCR buffer, 1 mM $MgSO_4$, the primers (15 pmol each), and 0.2 mM dNTPs (each produced by TOYOBO Co., Ltd.) by means of iCycler (BioRad) with the use of the genomic DNA as a template. Then, an amplified fragment with a size of approximately 1,500 by was collected, followed by digestion with EcoRI and PstI. Thus, a DNA fragment was obtained.

In addition, DNA fragments each encoding propionyl CoA transferase were obtained from *S. aureus* (ATCC10832) and *C. propionicum* (ATCC25522) in the manner described above. The following are PCR amplification conditions used herein: a PCR reaction (enzyme KOD-PLUS) of 1 cycle of 94° C. for 1 minute, 30 cycles of 94° C. for 30 seconds, 50° C. for 30 seconds, and 72° C. for 2 minutes, and 94° C. for 2 minutes.

The following are the sequences for the primer sets used for amplification of individual genes:

*M. elsdenii* PCT:

MePCTN:

5'-atgagaaaagtagaaatcattac-3'

MePCTC:

5'-ttattttttcagtcccatgggaccgtcctg-3'

-continued

```
C. propionicum PCT:
CpPCTN:
5'-gggggccatgggaaaggttcccattattaccgcagatgag -3'

CpPCTC:
5'-ggggggctcgagtcaggacttcatttccttcagacccat-3'

S. aureus PCT:
SpctN:
5'-gtgccatggaacaaatcacatggcacgac-3'

SpctC:
5'-cacgaattcatactttatgaattgattg-3'
```

Plasmid pTV118N (Takara Shuzo Co., Ltd.) was digested with EcoRI and PstI, followed by dephosphorylation with alkaline phosphatase. Subsequently, ligation was performed with the addition of the *M. elsdenii*-derived DNA fragment. Thus, a recombinant plasmid PTV118N M.E.-PCT with a size of approximately 4.7 kbp containing DNA encoding propionyl CoA transferase was prepared.

Similarly, the *C. propionicum*-derived and *S. aureus*-derived PCT genes are separately introduced into the NcoI-BamHI site and the NcoI-EcoRI site of a pTV118N vector (Takara Shuzo Co., Ltd.). Thus, PTV118N C.P.-PCT and PTV118N S.A.-PCT expression plasmids were produced.

According to the method described by Takase et al. (J. Biochem., 2003, vol. 133, pp. 139-145), a plasmid pGEMC1 (ST/QK)AB containing DNAs encoding STQK was prepared.

pGEMC1(ST/QK)AB was digested with BamHI to collect a DNA fragment with a size of approximately 6 kbp. T4 polymerase (200 units) was allowed to act at 37° C. for 5 minutes in a 3 mM Tris acetate buffer solution (pH 7.9) containing 66 mM potassium acetate, 10 mM magnesium acetate, 0.5 mM DTT, 0.1 mg/mL BSA, and 0.1 mM dNTP. Thus, a DNA fragment encoding STQK was obtained.

pTV118N M.E.-PCT was digested with PstI. T4 polymerase was allowed to act under the conditions described above, followed by dephosphorylation with alkaline phosphatase. The above DNA fragment encoding phaCm was subjected to ligation. DNA encoding STQK was introduced to the SalI site of pTV118N M.E.-PCT. Thus, plasmid pTV118N-PCT-C1(ST/QK)AB (approximately 9.6 kbp) was obtained. pTV118N-PCT-C1 was obtained by amplifying the region excluding phaA and phaB of pTV118N-PCT-C1AB by PCR, followed by self-ligation of the amplified product (FIG. 1). *Escherichia* sp. W3110 competent cells were transformed using pTV118N-PCT-C1(ST/QK).

In addition, pTV118N-C.P PCT-C1(STQK) having the DNA fragment encoding phaCm was obtained using the PTV118N C.P.-PCT expression plasmid in the manner described above, followed by transformation of *Escherichia* sp. W3110 competent cells.

(2) Polymer Production

For culture of the obtained transformant, active colonies formed on the LB agar medium were inoculated onto an LB liquid medium (10 ml) contained in a 100-ml Erlenmeyer flask and subjected to shake culture at 30° C. until OD 0.6 to 1.0 was reached (IFM (130 rpm); Oriental Giken Inc.). The preculture solution of grown bacterial cells was inoculated onto a medium for main culture (200 ml) contained in a 500-ml Erlenmeyer flask so that it accounted for 1% of the resultant, followed by shake culture.

After culture in the 200-ml medium by the method described above, bacterial cells were collected from the obtained culture solution using a 50-ml Falcon tube (3000×g, 5 min, RT), followed by overnight freezing at −80° C. The frozen bacterial cells were dried by a lyophilizer (LABCONCO, Model 77400) for 2 days.

The dried bacterial cells were placed in a pressure-proof test tube. Chloroform was added thereto in an amount of 1 ml per 100 mg of bacterial cells, followed by reflux in a water bath at 95° C. for 3 hours. The sample subjected to reflux was cooled to room temperature, filtered with a 0.22-Mm PTFE filter, and introduced into a silicone centrifugal tube for removal of bacterial cells. The extracted sample was dried at room temperature until chloroform was completely removed therefrom. Hexane (2 ml) was added to the pellet obtained after drying, followed by vortexing for approximately 1 minute and centrifugation (6,000×g, 15 minutes, RT) for removal of the supernatant. Washing with hexane was carried out twice in such manner. The dried sample was dissolved in chloroform (2 ml). The resultant was placed in a glass vial and dried. The resultant was designated as a polymer analysis sample.

(3) Polymer Analysis (i) GPC

Chloroform (1 mL) was added to the polymer (approximately 1 mg) collected in (2) above, followed by filtration with a 0.2-μm PTFE filter (ADVANTEC). The resulting solution was used as a sample and subjected to determination by GPC under the conditions described below.

System: Shimadzu Prominence GPC System

Column: TSKgel-Super THZ-M (6.0 mm×150 mm)

Eluent: $CHCl_3$

Flow rate: 0.8 mL/minute

Temperature: 40° C.

Detection: 10A refractive index detector

Sample amount: 10 μL

Figure 2:
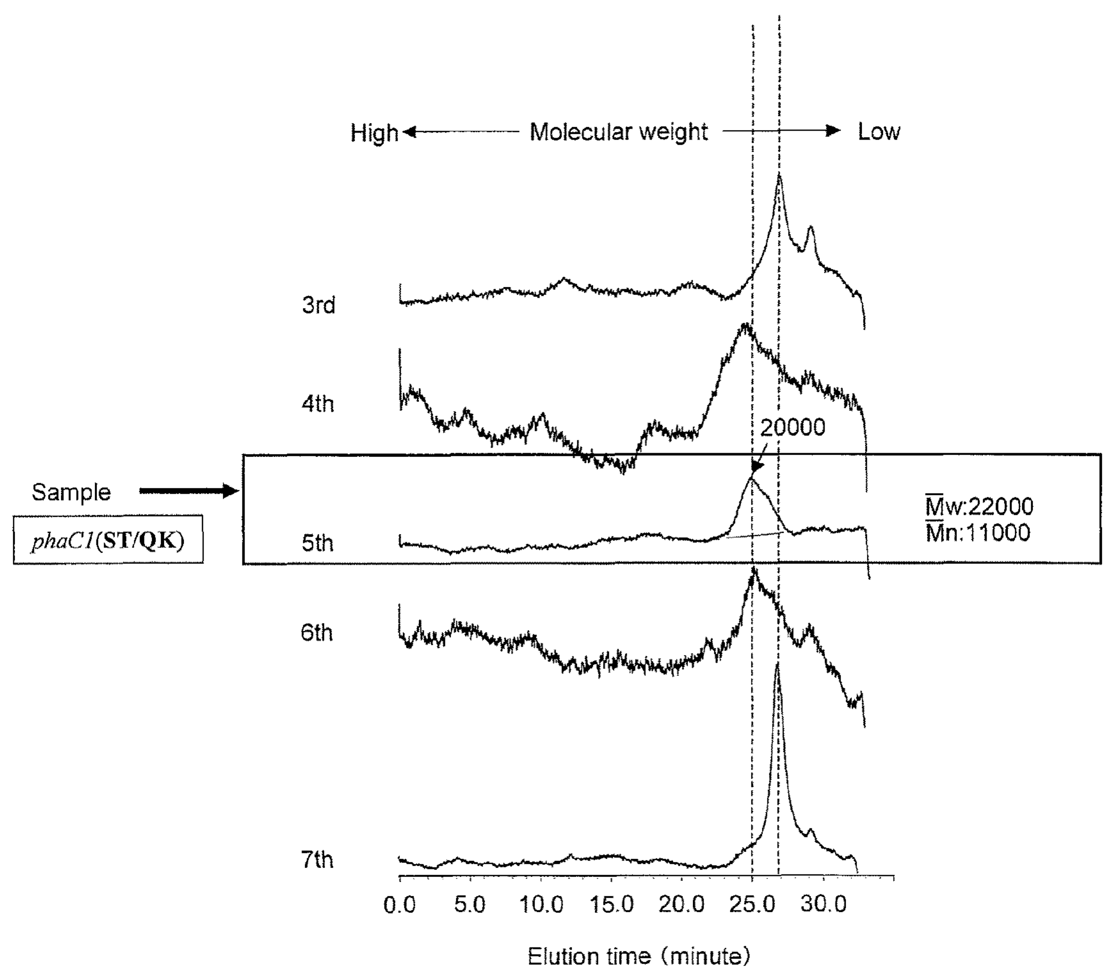
FIG. 2 shows a molecular weight distribution curve for the polymer prepared in the Example.

FIG. 2 shows a distribution curve of determined molecular weights. A molecular weight calibration curve was created with the use of a standard polystyrene. The molecular weight was represented by a value converted to the standard polystyrene molecular weight. As a result, the polymer molecular weight (mW) was 22,000.

(ii) GC/MS Analysis

After culture in the 200-ml medium by the method described above, bacterial cells were collected from the obtained culture solution using a 50-ml Falcon tube (3000×g, 5 min, RT), followed by overnight freezing at −80° C. The frozen bacterial cells were dried by a lyophilizer (LABCONCO, Model 77400) for 2 days. Then, 100 mg of the dried bacterial cells were weighed and placed in a pressure-proof test tube. Chloroform (1.6 ml) was added thereto and the resultant was allowed to stand still overnight at room temperature. A methanol-sulfuric acid mixture (a liquid mixture; methanol:sulfuric acid=17:3) (1.6 ml) was added to the bacterial cell/chloroform solution. An internal standard (100 μl) (benzoic acid: 10 mg/$CHCl_3$: 10 ml) was added thereto, followed by reflux in a water bath at 95° C. for 3 hours for methylation. After the end of methylation, the sample was cooled to room temperature and placed in a disposable test tube (ϕ: 18 mm). Milli-Q water (800 μl) was added thereto, followed by stirring for approximately 30 seconds. Thereafter, the resultant was allowed to stand still until it was separated into an aqueous layer and a solvent layer. After separation, the chloroform layer was sampled with a Pasteur pipette, filtered with a 0.22-μm PTFE filter, and introduced into a 2-ml vial for analysis.

Methylation of a polylactate authentic preparation was carried out in the following manner. First, PLA-0020 (Wako Pure Chemical Industries, Ltd.; weight-average molecular weight: 20,000) (20 mg) was dissolved in chloroform (10 ml) in a 20-ml vial. A portion of the resultant (1 ml) was placed in a pressure-proof test tube. Chloroform (0.6 ml), methanol sulfuric acid (1.6 ml), and an internal standard (100 μl) were added thereto, followed by reflux in a water bath at 95° C. for 3 hours. After the end of methylation, the standard sample was cooled to room temperature and placed in a disposable test tube (ϕ: 18 mm). Milli-Q water (800 μl) was added thereto and the resultant was stirred for approximately 30 seconds. The resultant was allowed to stand still until it was separated into an aqueous layer and a solvent layer. After separation, a chloroform layer was introduced into a 2-ml vial with the use of a Pasteur pipette, and the resultant was used for analysis.

GC/MS analysis was performed under the conditions described below.

The methylated product was analyzed using a GC/MS (HP6890 Series GC system/5973 Mass SelectiveDetector) equipped with an Agilent DB-1 column (122-10G3; 150 meters×0.25 mm×1 mm) or an Agilent DB-1 column (122-1063; 60 meters×0.25 mm×1 mm). The analysis methods implemented with the use of the columns are described below.

Figure 3A:
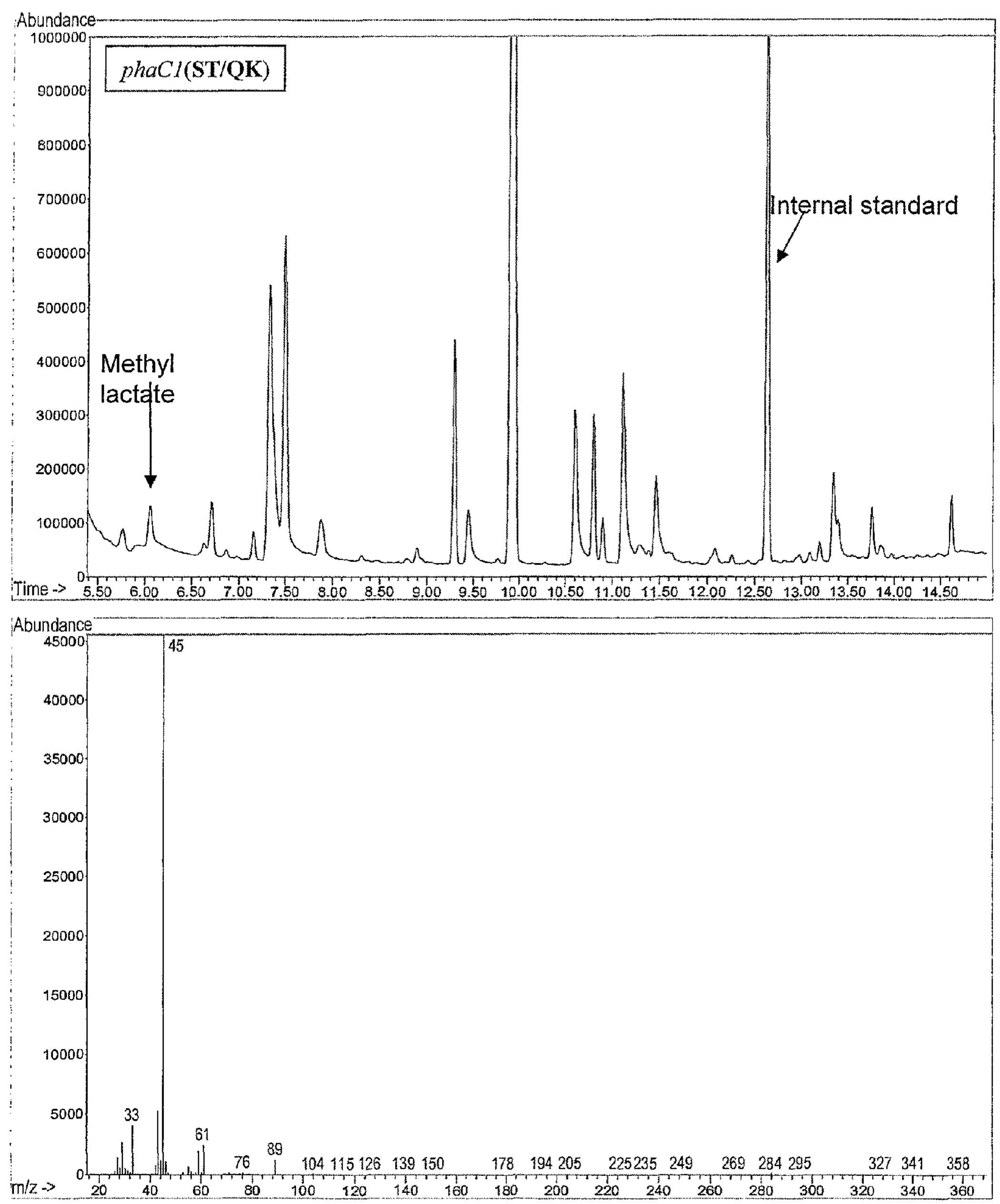
FIG. 3A is a chart showing GC/MS analysis results for the polymer prepared using a recombinant plasmid pTV118NPCTC1(ST/QK) having the *M. elsdenii*-derived PCT gene and the phaC1(ST/QK) gene.
Figure 3B:
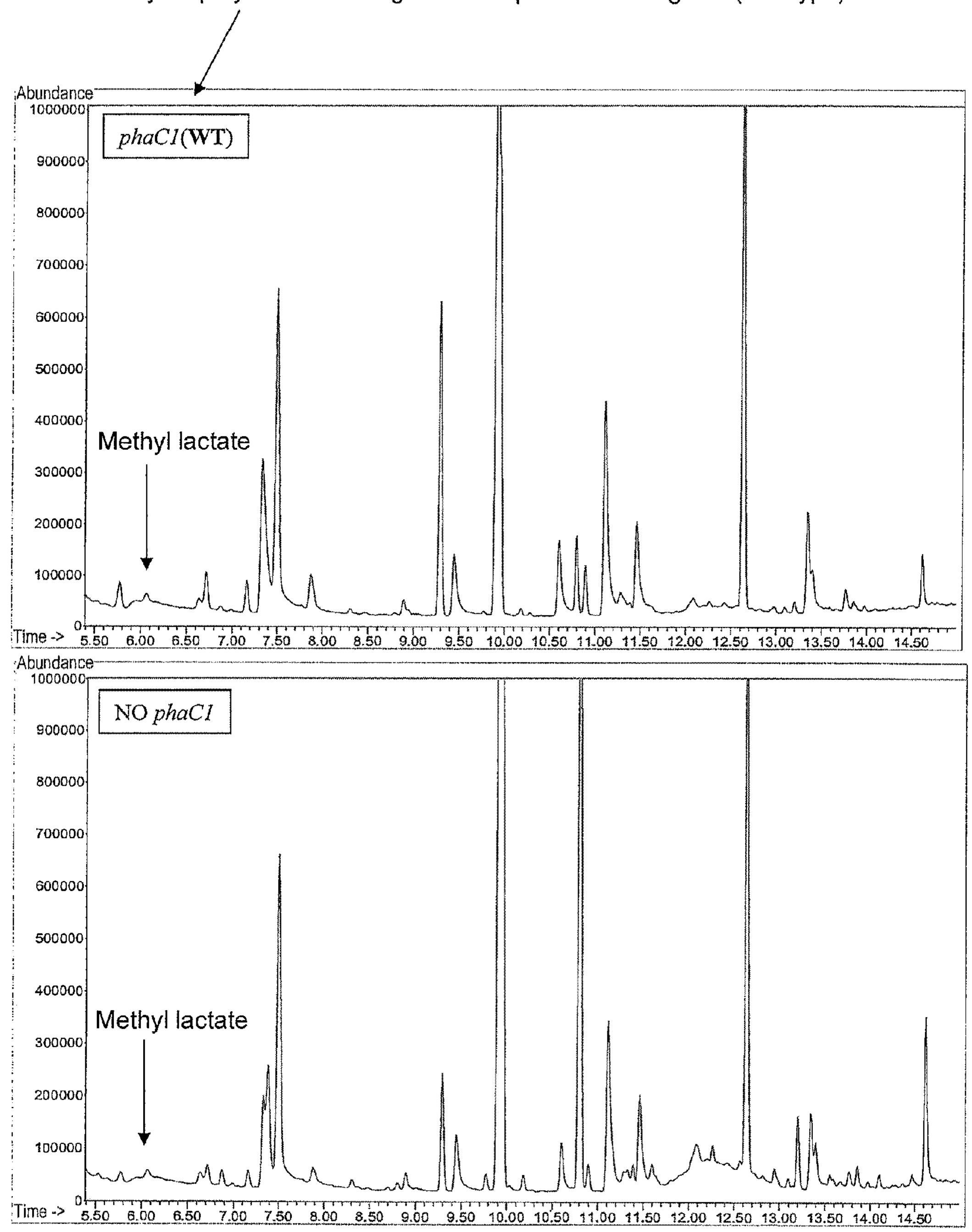
FIG. 3B is a chart showing GC/MS analysis results for the polymer prepared using a recombinant plasmid pTV118NPCTC1(WT) having The *M. elsdenii*-derived PCT gene and the phaC1(WT) gene.
Figure 3C:
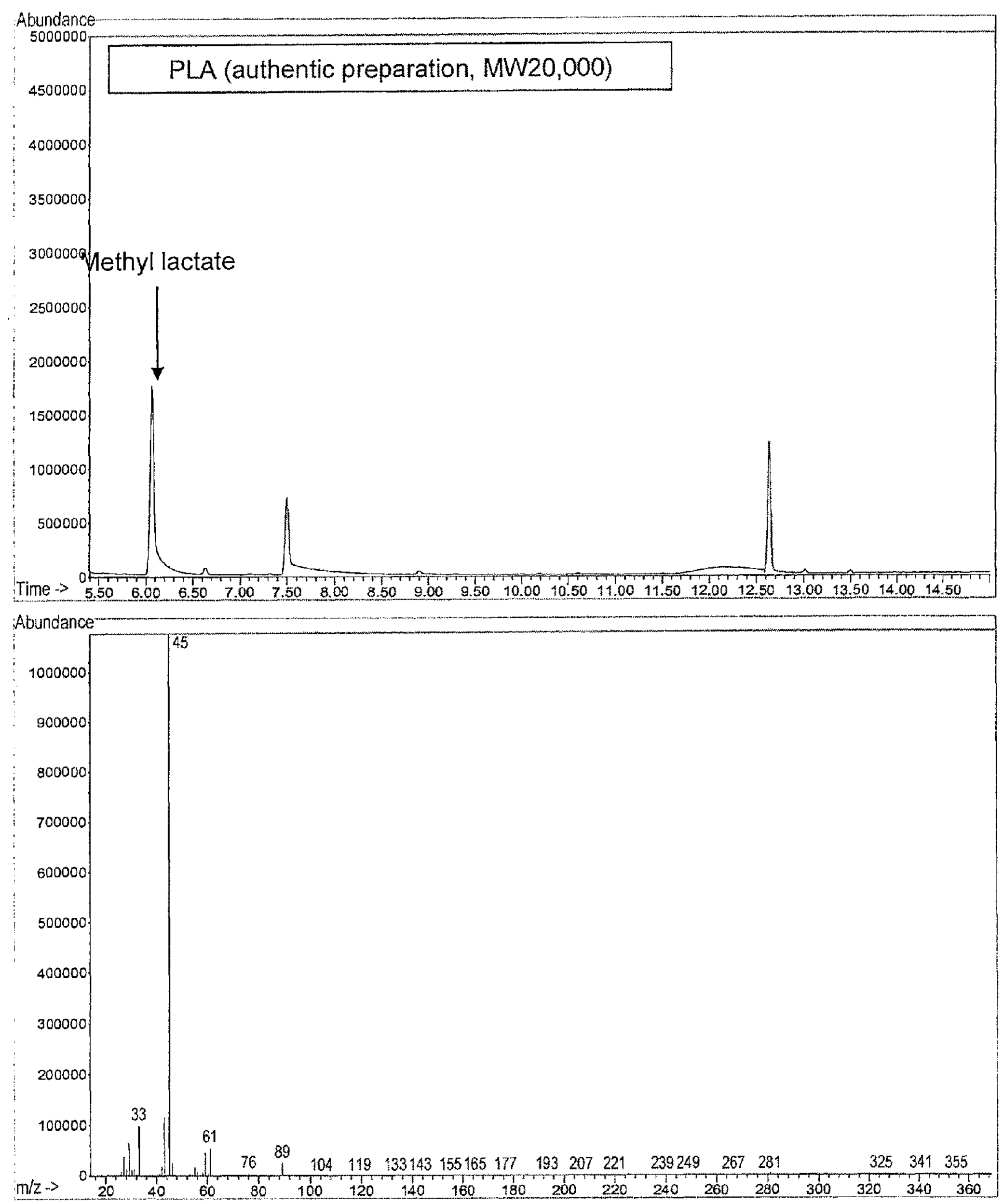
FIG. 3C is a chart showing GC/MS analysis results for the polymer prepared using a PLA authentic preparation (MW20,000).
Figure 3D:
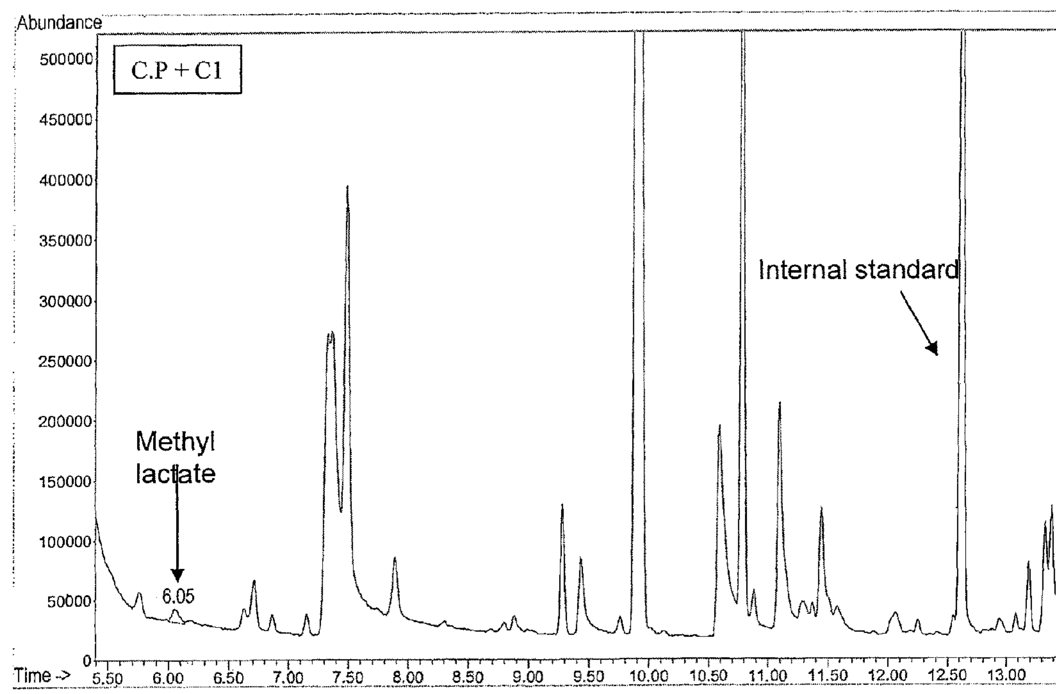
FIG. 3D is a chart showing GC/MS analysis results for the polymer prepared using a recombinant plasmid pTV118NPCTC1(ST/QK) having the *M. elsdenii*-derived PCT gene or the *C. propionicum*-derived PCT gene and the phaC1(ST/QK) gene.
Figure 3D:
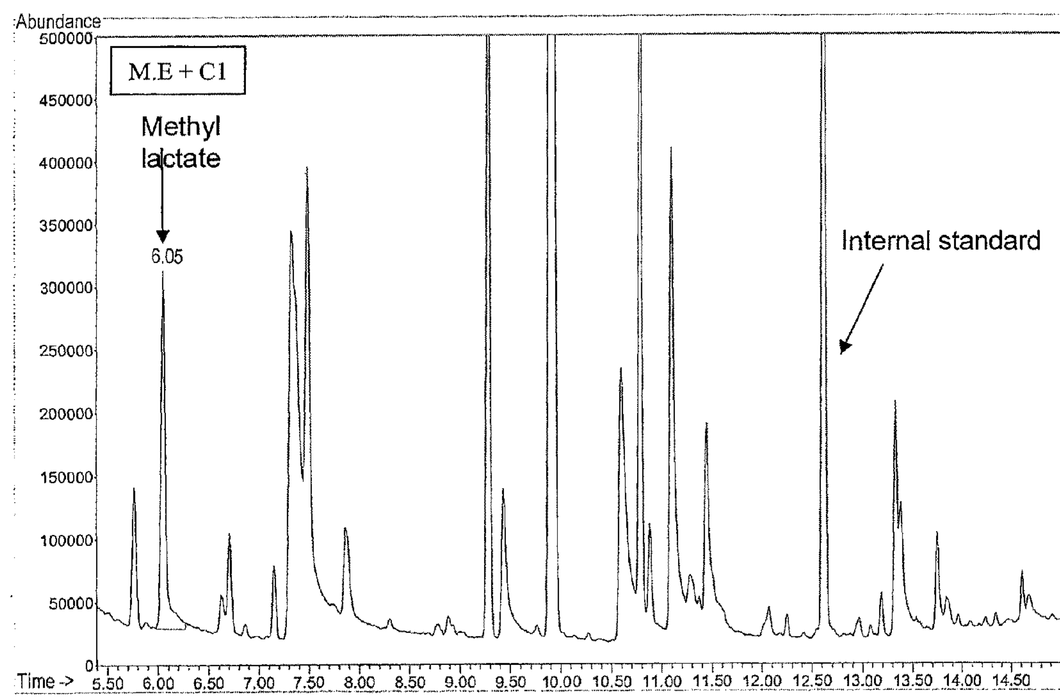

122-10G3: Holdup at 150° C. for 2 minutes; temperature increase at a rate of 5° C./1 minute; and holdup at 300° C. for 10 minutes 122-1063: Holdup at 120° C. for 5 minutes; temperature increase at a rate of 5° C./1 minute; and holdup at 300° C. for 10 minutes FIGS. 3A to 3D each show analysis results obtained under the above conditions and the MS spectrum for methyl lactate. Note that, only the results shown in FIG. 3D were obtained from the sample from which no chloroform had been removed. As a result of GC/MS, the polymer collected in (2) was confirmed to contain LA as a monomer unit.

(iii) NMR Analysis

Figure 4:
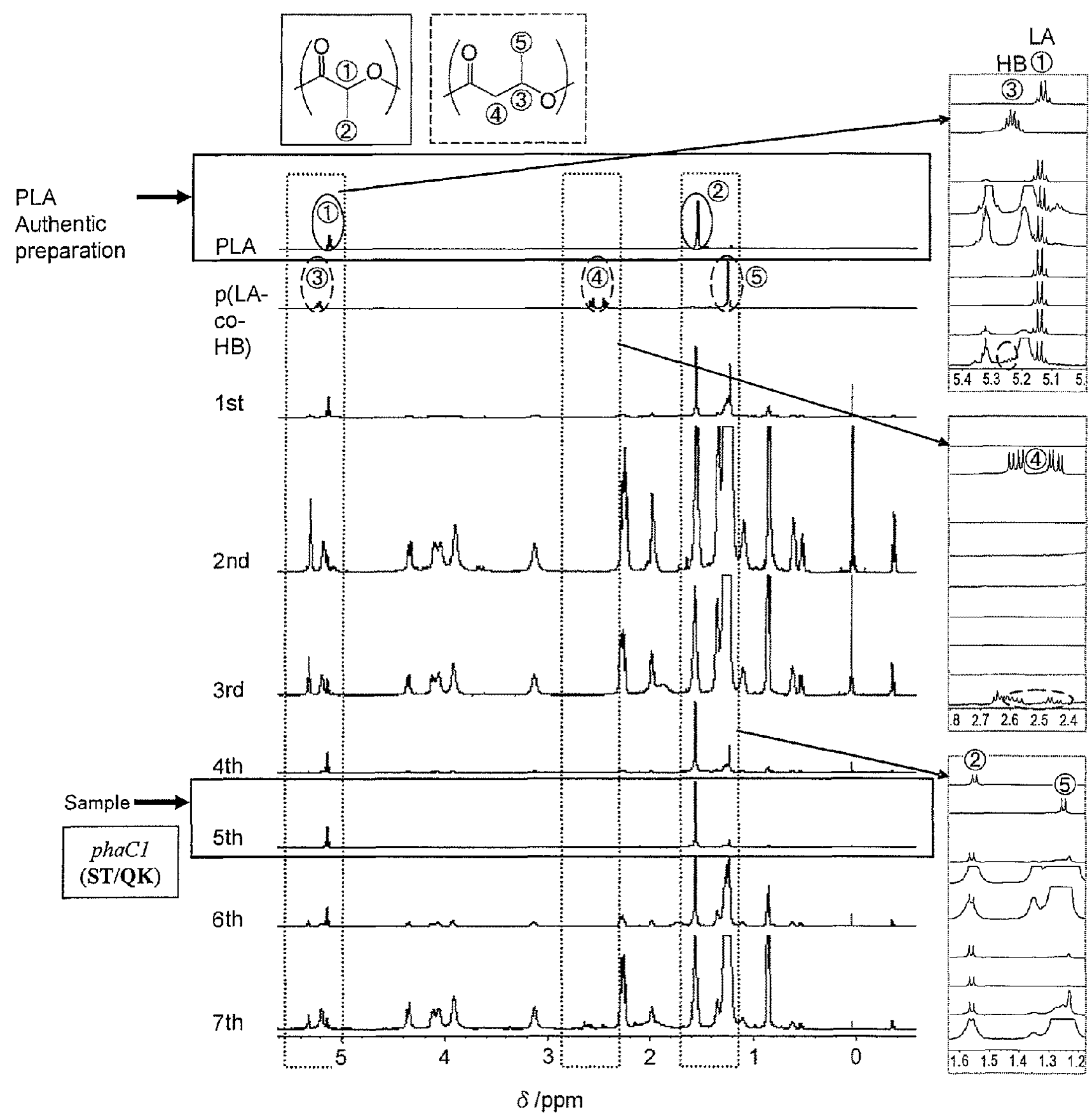
FIG. 4 is a chart showing H-NMR spectral analysis results for the polymer prepared in the Example.

A sample was prepared by dissolving the polymer collected in (2) in deuterated chloroform, followed by $^{1}$H-NMR (FIG. 4) determination at 300 MHz. As a result, it was found that the polymer collected in (2) contained lactate as a monomer unit.

(4) PCT Expression and Lactoyl CoA Synthesis in Microorganisms

The PTV118N M.E.-PCT, PTV118N C.P.-PCT, and PTV118N S.A.-PCT recombinant plasmids produced in (1) were used for transformation of *Escherichia* sp. W3110 competent cells.

After preculture, each cell line was inoculated onto a 200-ml LB medium contained in a 2-L flask so as to result in a content of 2%, followed by culture at 37° C. at 180 rpm for 3 hours. Expression was induced using 10 mM IPTG at approximately OD600=0.5, followed by culture at 30° C. at 80 rpm for 6 hours. Next, bacterial cells were collected via centrifugation, followed by culture at 37° C. in M9 (+1.5% glucose, 10 mM $MgSO_4$, 10 mM calcium pantothenate) (OD=20; 3 ml), followed by sampling in an appropriate manner.

Bacterial cells (approximately $1\times10^5$ cells) were collected for sample preparation (n=3). The sample was applied to a suction filter system and washed twice with Milli-Q water. A filter was placed (face down) in a petri dish containing an MeOH solution (2 ml) and left at room temperature for 10 minutes. Then, the MeOH solution (1.6 ml) was introduced into a centrifugal tube. Chloroform (1.6 ml) and Milli-Q water (640 ul) were mixed together and suspended, followed by centrifugation at 4600 g at 4° C. for 5 min. The water+MeOH layer (1.5 ml) was subjected to centrifugal filtration using a 5 k ultrafiltration membrane (Millopore) for approximately 2 hours. The filtrate was collected and lyophilized. The resultant was concentrated 200-fold and dissolved in Milli-Q water containing a secondary internal standard substance, followed by CE-MS analysis. CE-MS analysis conditions were determined in accordance with Anal. Chem. 2002, 74, 6224-6229, "Pressure-Assisted Capillary Electrophoresis Electrospray Ionization Mass Spectrometry for Analysis of Multivalent Anions." FIG. 6 shows the results.

Figure 6:
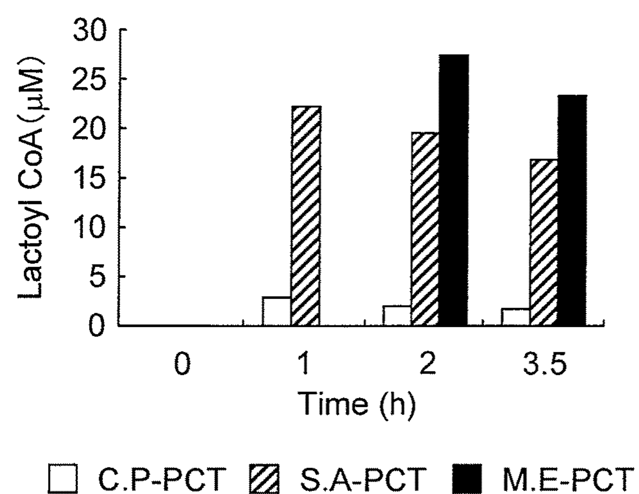
FIG. 6 is a graph showing time-dependent changes in lactoyl CoA production in accordance with different PCT genes.

Based on FIG. 6, it has been revealed that the *S. aureus*-derived PCT gene exhibits lactate CoA productivity at a level greater than that of the *M. elsdenii*-derived PCT gene in the early phase of culture.

(5) Influence of the PCT Gene upon Polylactate Productivity

Figure 7:
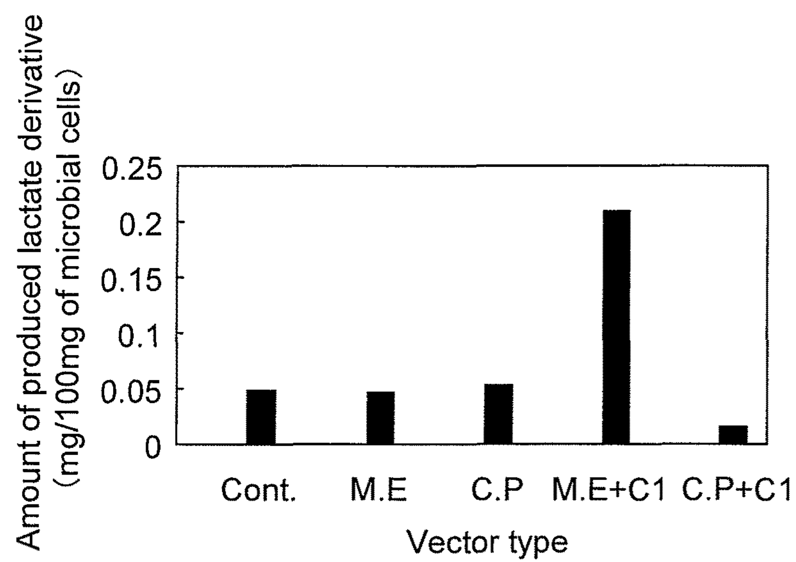
FIG. 7 is a graph showing a comparison in terms of polylactate productivity between the *M. elsdenii*-derived PCT gene and the *C. propionicum*-derived PCT gene.

FIG. 7 shows quantification results for a lactate derivative obtained by GC/MS analysis in (ii) above.

Based on the results shown in FIG. 7, it has been revealed that *M. elsdenii*-derived PCT is superior to *C. propionicum*-derived PCT in terms of favorable contribution to polylactate productivity.

Comparative Example

Figure 5:
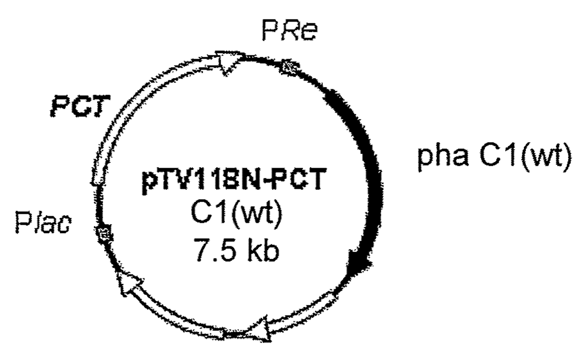
FIG. 5 schematically shows the configuration of a recombinant plasmid pTV118NPCTC1(WT). In the figure, "phaC1 (WT)" denotes *Pseudomonas* sp. 61-3-derived polyhydroxyalkanoate synthase gene (wild type), "PCT" denotes the *M. elsdenii*-derived PCT gene, "PRe" denotes an *Alcaligenes eutrophus*-derived promoter, and "Plac" denotes a lactose operon promoter.

An expression vector was prepared by replacing the nucleotide sequence encoding STQK contained in the pTV118N-PCT-C1(ST/QK) plasmid produced in Example 1 with the nucleotide sequence encoding the protein described below. FIG. 5 shows an outline of the construction of the expression vector.

pTV118N-PCT-C1(WT): Polyhydroxyalkanoate synthase of *Pseudomonas* sp. 61-3 (wild type; SEQ ID NO: 1)

*Escherichia coli* W3110 competent cells were transformed using pTV118N-PCT-C1. For culture of the obtained transformant, active colonies formed on the LB agar medium were inoculated onto an LB liquid medium (10 ml) contained in a 100-ml Erlenmeyer flask, followed by shake culture at 30° C. to result in OD 0.6 to 1.0 (IFM (130 rpm); Oriental Giken Inc.). The grown precultured cell solution was inoculated to a content of 1% on a medium for main culture (200 ml) contained in a 500-ml Erlenmeyer flask, followed by shake culture.

After culture in the 200-ml medium by the method described above, bacterial cells were collected from the obtained culture solution using a 50-ml Falcon tube (3000×g, 5 min, RT), followed by overnight freezing at −80° C. The frozen bacterial cells were dried by a lyophilizer (LABCONCO, Model 77400) for 2 days. Then, 100 mg of the dried bacterial cells were weighed and introduced into a pressure-proof test tube. Chloroform (1.6 ml) was added thereto and the resultant was allowed to stand still overnight at room temperature. Methanol sulfuric acid (1.6 ml) and an internal standard (100 μl) (benzoic acid: 10 mg/$CHCl_3$: 10 ml) were added to the bacterial cells/chloroform solution. The resultant was subjected to reflux in a water bath at 95° C. for 3 hours for methylation. After the end of methylation, the sample was cooled to room temperature and introduced into a disposable test tube (ϕ: 18 mm), Milli-Q water (800 μl) was added thereto and the resultant was stirred for approximately 30 seconds. The resultant was allowed to stand still until it was separated into an aqueous layer and a solvent layer. After separation, a chloroform layer was collected using a Pasteur pipette and filtered with a 0.22-μm PTFE filter into a 2-ml vial, followed by GS/MS analysis.

GS/MS analysis was performed in the manner described in Example 1. Based on the results shown in FIG. 3B, it was confirmed that substantially no polymer containing lactate can be produced using pTV118NPCTC1(WT).

All publications, patents, and patent applications cited herein are incorporated herein by reference in their entirety.

---

The invention claimed is:

1. A method for producing a polylactate, which comprises the steps of:

(1) culturing a recombinant microorganism having a protein capable of catalyzing a reaction of transferring CoA to propionic acid and/or lactate consisting of the amino acid sequence shown in SEQ ID NO: 4 or 6 and a protein capable of catalyzing a reaction of polyhydroxyalkanoate synthesis consisting of an amino acid sequence derived from the amino acid sequence shown in SEQ ID NO: 2 by substitution of at least one of the amino acids at positions 130, 325, 477, and 481 with different amino acid(s); and (2) collecting the polylactate from the culture product obtained in step (1).

2. The production method according to claim 1, wherein the amino acid sequence of the protein capable of catalyzing a reaction of polyhydroxyalkanoate synthesis is an amino acid sequence derived from the amino acid sequence shown in SEQ ID NO: 2 by substitution of amino acids at positions 325 and 481 with different amino acids.

3. The production method according to claim 1, wherein the amino acid sequence of the protein capable of catalyzing a reaction of polyhydroxyalkanoate synthesis is an amino acid sequence derived from the amino acid sequence shown in SEQ ID NO: 2 by substitution of Ser at position 325 with Thr and Gln at position 481 with Lys.

4. The production method according to claim 1, wherein any one of the proteins is a protein encoded by a recombinant expression vector introduced into a microorganism.

5. A recombinant microorganism having a protein capable of catalyzing a reaction of transferring CoA to propionic acid and/or lactate consisting of the amino acid sequence shown in SEQ ID NO: 4 or 6 and a protein capable of catalyzing a reaction of polyhydroxyalkanoate synthesis consisting of an amino acid sequence derived from the amino acid sequence shown in SEQ ID NO: 2 by substitution of at least one of the amino acids at positions 130, 325, 477, and 481 with different amino acid(s).

6. The recombinant microorganism according to claim 5, wherein the amino acid sequence of the protein capable of catalyzing a reaction of polyhydroxyalkanoate synthesis is an amino acid sequence derived from the amino acid sequence shown in SEQ ID NO: 2 by substitution of amino acids at positions 325 and 481 with different amino acids.

7. The recombinant microorganism according to claim 5, wherein the amino acid sequence of a protein capable of catalyzing a reaction of polyhydroxyalkanoate synthesis is an amino acid sequence derived from the amino acid sequence shown in SEQ ID NO: 2 by substitution of Ser at position 325 with Thr and Gln at position 481 with Lys.

8. The recombinant microorganism according to claim 5, into which a recombinant expression vector having a gene encoding any one of the proteins is introduced.

* * * * *